US009449296B2

(12) United States Patent
MacDonald et al.

(10) Patent No.: US 9,449,296 B2
(45) Date of Patent: Sep. 20, 2016

(54) MANAGEMENT OF PHARMACY KITS USING MULTIPLE ACCEPTANCE CRITERIA FOR PHARMACY KIT SEGMENTS

(71) Applicant: Kit Check, Inc., Washington, DC (US)

(72) Inventors: Kevin William MacDonald, Washington, DC (US); David Mario Pedra, Washington, DC (US); Timothy James Leo Kress-Spatz, Washington, DC (US); Christian Doyle, Silver Spring, MD (US); Eric Brody, Reston, VA (US)

(73) Assignee: Kit Check, Inc., Washington, DC (US)

( * ) Notice: Subject to any disclaimer, the term of this patent is extended or adjusted under 35 U.S.C. 154(b) by 16 days.

(21) Appl. No.: 14/472,410

(22) Filed: Aug. 29, 2014

(65) Prior Publication Data
US 2014/0372145 A1 Dec. 18, 2014

Related U.S. Application Data

(63) Continuation-in-part of application No. 13/554,342, filed on Jul. 20, 2012, now Pat. No. 8,990,099.

(60) Provisional application No. 62/021,927, filed on Jul. 8, 2014, provisional application No. 61/514,231, filed on Aug. 2, 2011.

(51) Int. Cl.
*G06Q 50/22* (2012.01)
*G06Q 50/24* (2012.01)
*G06Q 10/08* (2012.01)

(52) U.S. Cl.
CPC .......... *G06Q 10/0875* (2013.01); *G06Q 50/22* (2013.01); *G06Q 50/24* (2013.01)

(58) Field of Classification Search
CPC ............................. G06Q 50/22; G06Q 50/24

USPC .......................................................... 705/2–3
See application file for complete search history.

(56) References Cited

U.S. PATENT DOCUMENTS

| 5,713,485 | A | 2/1998 | Liff et al. |
| 5,930,145 | A | 7/1999 | Yuyama et al. |
| 5,986,662 | A | 11/1999 | Argiro et al. |
| 6,112,502 | A | 9/2000 | Frederick et al. |

(Continued)

FOREIGN PATENT DOCUMENTS

| CA | 27223828 | 10/2009 |
| CA | 2 790 220 | 6/2013 |

(Continued)

OTHER PUBLICATIONS

Barlas, Stephen, "Pharmacy Product Tracing Likely to Go National—Costs to Pharmacies Worrisome," Pharmacy & Therapeutics, Jan. 2009, vol. 34 No. 1, p. 14.
Cakici, O.E., et al., "Using RFID for the management of pharmaceutical inventory-system optimization and shrinkage control," Decision Support Systems, 2011, pp. 842-852.
CPG Sec. 400.210, Radiofrequency Identification Feasibility Studies and Pilot Programs for Drugs Nov. 2004 Compliance Policy Guide available at: http://www.fda.gov/ICECl/ComplianceManuals/CompliancePolicyGuidanceManual/ucm074357.htm.

(Continued)

*Primary Examiner* — Eliza Lam
(74) *Attorney, Agent, or Firm* — Knobbe, Martens, Olson & Bear, LLP

(57) ABSTRACT

A pharmacy kit is managed by defining multiple rules for determining whether a segment of a pharmacy kit is satisfactorily stocked, selecting at least one rule among the multiple rules according to a kit stocking contingency, an prompting a user to stock the segment of the pharmacy kit according to the selected at least one rule.

20 Claims, 27 Drawing Sheets

(56) References Cited

U.S. PATENT DOCUMENTS

| | | |
|---|---|---|
| 6,249,299 B1 | 6/2001 | Tainer |
| 6,275,157 B1 | 8/2001 | Mays et al. |
| 6,294,999 B1 | 9/2001 | Yarin et al. |
| 6,574,166 B2 | 6/2003 | Niemiec |
| 6,632,619 B1 | 10/2003 | Harrison et al. |
| 6,771,369 B2 | 8/2004 | Rzasa et al. |
| 6,825,864 B2 | 11/2004 | Botten et al. |
| 6,851,615 B2 | 2/2005 | Jones |
| 6,877,658 B2 | 4/2005 | Raistrick et al. |
| 6,900,021 B1 | 5/2005 | Harrison et al. |
| 6,933,849 B2 | 8/2005 | Sawyer |
| 6,935,560 B2 | 8/2005 | Andreasson et al. |
| 6,952,681 B2 | 10/2005 | McQuade et al. |
| 6,985,870 B2 | 1/2006 | Martucci et al. |
| 6,994,249 B2 | 2/2006 | Peterka et al. |
| 7,061,831 B2 | 6/2006 | De La Huerga |
| 7,116,343 B2 | 10/2006 | Botten et al. |
| 7,118,029 B2 | 10/2006 | Nycz et al. |
| 7,140,542 B2 | 11/2006 | Andreasson et al. |
| 7,146,247 B2 | 12/2006 | Kirsch et al. |
| 7,151,456 B2 | 12/2006 | Godfrey |
| 7,158,030 B2 | 1/2007 | Chung |
| 7,165,077 B2 | 1/2007 | Kalies |
| 7,175,081 B2 | 2/2007 | Andreasson et al. |
| 7,177,721 B2 | 2/2007 | Kirsch et al. |
| 7,182,256 B2 | 2/2007 | Andreasson et al. |
| 7,212,100 B2 | 5/2007 | Terenna |
| 7,227,469 B2 * | 6/2007 | Varner et al. .............. 340/572.1 |
| 7,232,066 B2 | 6/2007 | Andreasson et al. |
| 7,253,736 B2 | 8/2007 | Tethrake et al. |
| 7,256,699 B2 | 8/2007 | Tethrake et al. |
| 7,264,323 B2 | 9/2007 | Tainer et al. |
| 7,268,684 B2 | 9/2007 | Tethrake et al. |
| 7,275,645 B2 * | 10/2007 | Mallett et al. ................ 209/702 |
| 7,299,981 B2 | 11/2007 | Hickle et al. |
| 7,318,579 B1 * | 1/2008 | Novoa ........................... 254/278 |
| 7,341,147 B2 | 3/2008 | Mallett et al. |
| 7,354,884 B2 | 4/2008 | Hada et al. |
| 7,362,228 B2 | 4/2008 | Nycz et al. |
| 7,375,737 B2 | 5/2008 | Botten et al. |
| 7,394,383 B2 | 7/2008 | Hager et al. |
| 7,440,818 B2 | 10/2008 | Handfield et al. |
| 7,446,747 B2 | 11/2008 | Youngblood et al. |
| 7,454,880 B1 | 11/2008 | Austin et al. |
| 7,486,188 B2 | 2/2009 | Van Alstyne |
| 7,492,257 B2 | 2/2009 | Tethrake et al. |
| 7,492,261 B2 | 2/2009 | Cambre et al. |
| 7,504,954 B2 | 3/2009 | Spaeder |
| 7,518,502 B2 | 4/2009 | Austin et al. |
| 7,551,089 B2 | 6/2009 | Sawyer |
| 7,559,483 B2 | 7/2009 | Hickle et al. |
| 7,564,364 B2 | 7/2009 | Zweig |
| 7,639,136 B1 | 12/2009 | Wass et al. |
| 7,644,016 B2 | 1/2010 | Nycz et al. |
| 7,672,872 B2 | 3/2010 | Shanton |
| 7,706,915 B2 | 4/2010 | Mohapatra et al. |
| 7,706,916 B2 | 4/2010 | Hilton |
| 7,712,670 B2 | 5/2010 | Sauerwein, Jr. et al. |
| 7,715,277 B2 | 5/2010 | De La Huerga |
| 7,729,597 B2 | 6/2010 | Wright et al. |
| 7,734,157 B2 | 6/2010 | Wright et al. |
| 7,747,477 B1 | 6/2010 | Louie et al. |
| 7,752,085 B2 | 7/2010 | Monroe |
| 7,772,964 B2 | 8/2010 | Tethrake et al. |
| 7,775,056 B2 | 8/2010 | Lowenstein |
| 7,783,163 B2 | 8/2010 | Wright et al. |
| 7,783,174 B2 | 8/2010 | Wright et al. |
| 7,801,422 B2 | 9/2010 | Wright et al. |
| 7,815,117 B2 | 10/2010 | Tuschel et al. |
| 7,834,765 B2 | 11/2010 | Sawyer |
| 7,834,766 B2 | 11/2010 | Sawyer |
| 7,837,093 B1 | 11/2010 | Leu et al. |
| 7,837,107 B1 | 11/2010 | Leu et al. |
| 7,858,841 B2 | 12/2010 | Krautkramer et al. |
| 7,860,730 B1 | 12/2010 | Goodall et al. |
| 7,868,754 B2 | 1/2011 | Salvat, Jr. |
| 7,893,876 B2 | 2/2011 | Brown et al. |
| 7,908,030 B2 | 3/2011 | Handfield et al. |
| 7,918,830 B2 | 4/2011 | Langan et al. |
| 7,933,033 B2 | 4/2011 | Ohishi et al. |
| 7,976,508 B2 | 7/2011 | Hoag |
| 7,985,711 B2 | 7/2011 | Tohmatsu et al. |
| 7,990,272 B2 | 8/2011 | Wass et al. |
| 7,996,286 B2 | 8/2011 | Kreiner et al. |
| 8,002,174 B2 | 8/2011 | Coyne, III et al. |
| 8,006,903 B2 | 8/2011 | Braun et al. |
| 8,009,913 B2 | 8/2011 | Greyshock |
| 8,031,347 B2 | 10/2011 | Edwards et al. |
| 8,042,738 B2 | 10/2011 | Cloix |
| 8,049,627 B1 | 11/2011 | Addante |
| 8,063,925 B2 | 11/2011 | Tainer et al. |
| 8,065,858 B2 | 11/2011 | Leu et al. |
| 8,072,635 B2 | 12/2011 | Roberts et al. |
| 8,082,192 B2 | 12/2011 | Nycz et al. |
| 8,099,339 B1 | 1/2012 | Pinsonneault et al. |
| 8,108,068 B1 | 1/2012 | Boucher et al. |
| 8,111,159 B2 | 2/2012 | Andreasson et al. |
| 8,112,175 B2 | 2/2012 | Handfield et al. |
| 8,131,397 B2 | 3/2012 | Vahlberg et al. |
| 8,154,390 B2 | 4/2012 | Heath et al. |
| 8,174,392 B1 | 5/2012 | Sagbhini et al. |
| 8,186,587 B2 | 5/2012 | Zmood et al. |
| 8,212,677 B2 | 7/2012 | Ferguson |
| 8,219,413 B2 | 7/2012 | Martinez et al. |
| 8,224,483 B1 | 7/2012 | Ansari et al. |
| 8,231,749 B2 | 7/2012 | Dent et al. |
| 8,258,961 B2 | 9/2012 | Phillips et al. |
| 8,261,939 B2 | 9/2012 | Knoth |
| 8,279,069 B2 | 10/2012 | Sawyer |
| 8,283,287 B2 | 10/2012 | Aihara et al. |
| 8,284,059 B2 | 10/2012 | Ross |
| 8,285,083 B2 | 10/2012 | Canessa et al. |
| 8,285,607 B2 | 10/2012 | Danilewitz |
| 8,286,222 B2 | 10/2012 | Silverbrook et al. |
| 8,292,173 B2 | 10/2012 | Yturralde et al. |
| 8,292,186 B2 | 10/2012 | Deloche et al. |
| 8,296,950 B2 | 10/2012 | Colbrunn et al. |
| 8,328,082 B1 | 12/2012 | Bochenko et al. |
| 8,339,649 B2 | 12/2012 | Ohishi et al. |
| 8,341,041 B2 | 12/2012 | Hull |
| 8,346,632 B2 | 1/2013 | Saghbini |
| 8,355,753 B2 | 1/2013 | Bochenko et al. |
| 8,355,962 B2 | 1/2013 | Delaney et al. |
| 8,359,338 B2 | 1/2013 | Butterfield et al. |
| 8,376,228 B2 | 2/2013 | DeVet et al. |
| 8,384,545 B2 | 2/2013 | Hussain et al. |
| 8,385,972 B2 | 2/2013 | Bochenko et al. |
| 8,394,053 B2 | 3/2013 | Bochenko et al. |
| 8,403,212 B2 | 3/2013 | van Esch |
| 8,403,224 B2 | 3/2013 | Fedorko et al. |
| 8,405,508 B2 | 3/2013 | Burke |
| 8,461,076 B2 | 6/2013 | Okada et al. |
| 8,483,550 B2 | 7/2013 | Wright et al. |
| 8,509,604 B2 | 8/2013 | Wright et al. |
| 8,515,251 B2 | 8/2013 | Wright et al. |
| 8,519,849 B2 | 8/2013 | Ross-Messemer |
| 8,530,379 B2 | 9/2013 | Shimizu et al. |
| 8,564,416 B2 | 10/2013 | Steven et al. |
| 8,565,552 B2 | 10/2013 | Sommer et al. |
| 8,582,171 B2 | 11/2013 | Srnka et al. |
| 8,593,278 B2 | 11/2013 | Churbock et al. |
| 8,593,678 B2 | 11/2013 | Ohishi et al. |
| D694,817 S | 12/2013 | Adam et al. |
| 8,606,596 B1 | 12/2013 | Bochenko et al. |
| 8,636,202 B2 | 1/2014 | Keefe et al. |
| 8,639,525 B2 | 1/2014 | Levine et al. |
| 8,686,859 B2 | 4/2014 | Hussain et al. |
| 8,699,054 B2 | 4/2014 | Edwards et al. |
| 8,702,674 B2 | 4/2014 | Bochenko |
| 8,749,356 B2 | 6/2014 | Hussain et al. |
| 8,755,056 B2 | 6/2014 | Edwards et al. |
| 8,825,680 B2 | 9/2014 | Burke et al. |
| 8,922,435 B2 | 12/2014 | Fontecchio et al. |
| 8,945,066 B2 | 2/2015 | Bochenko et al. |

(56) References Cited

U.S. PATENT DOCUMENTS

| | | |
|---|---|---|
| 8,990,099 B2 | 3/2015 | MacDonald et al. |
| 9,037,479 B1 | 5/2015 | MacDonald et al. |
| 9,058,412 B2 | 6/2015 | MacDonald et al. |
| 9,058,413 B2 | 6/2015 | MacDonald et al. |
| 2002/0026330 A1 | 2/2002 | Klein |
| 2002/0087360 A1 | 7/2002 | Pettit |
| 2002/0087362 A1 | 7/2002 | Cobb et al. |
| 2002/0087554 A1 | 7/2002 | Seelinger |
| 2003/0055685 A1 | 3/2003 | Cobb et al. |
| 2003/0074223 A1 | 4/2003 | Hickle et al. |
| 2003/0160698 A1 | 8/2003 | Andreasson et al. |
| 2003/0216974 A1 | 11/2003 | Browne |
| 2004/0008123 A1 | 1/2004 | Carrender et al. |
| 2004/0032330 A1 | 2/2004 | Hoffman |
| 2004/0051368 A1 | 3/2004 | Caputo et al. |
| 2004/0057609 A1 | 3/2004 | Weinberg |
| 2004/0081669 A1 | 4/2004 | Greeven et al. |
| 2004/0178071 A1 | 9/2004 | Harrison et al. |
| 2004/0215486 A1 | 10/2004 | Braverman |
| 2004/0225528 A1 | 11/2004 | Brock |
| 2005/0014849 A1 | 1/2005 | Pettit et al. |
| 2005/0014948 A1 | 1/2005 | Pettit et al. |
| 2005/0060171 A1 | 3/2005 | Molnar |
| 2005/0062603 A1 | 3/2005 | Fuerst et al. |
| 2005/0108044 A1 | 5/2005 | Koster |
| 2005/0125097 A1 | 6/2005 | Chudy et al. |
| 2005/0127176 A1 | 6/2005 | Dickinson |
| 2005/0149378 A1 | 7/2005 | Cyr et al. |
| 2005/0184151 A1 | 8/2005 | DiMaggio et al. |
| 2005/0283259 A1 | 12/2005 | Wolpow |
| 2005/0285732 A1 | 12/2005 | Sengupta et al. |
| 2005/0285746 A1 | 12/2005 | Sengupta et al. |
| 2006/0006999 A1 | 1/2006 | Walczyk et al. |
| 2006/0043177 A1 | 3/2006 | Nycz et al. |
| 2006/0043179 A1 | 3/2006 | Nycz et al. |
| 2006/0065726 A1 | 3/2006 | Andreasson et al. |
| 2006/0109105 A1 | 5/2006 | Varner et al. |
| 2006/0132311 A1 | 6/2006 | Kruest et al. |
| 2006/0145871 A1 | 7/2006 | Donati et al. |
| 2006/0152338 A1 | 7/2006 | Hsu |
| 2006/0152364 A1 | 7/2006 | Walton |
| 2006/0152367 A1 | 7/2006 | Narayanaswamy |
| 2006/0267731 A1 | 11/2006 | Chen |
| 2007/0001809 A1 | 1/2007 | Kodukula et al. |
| 2007/0008399 A1 | 1/2007 | Botten et al. |
| 2007/0023512 A1* | 2/2007 | Miller et al. .............. 235/385 |
| 2007/0023513 A1 | 2/2007 | Andreasson et al. |
| 2007/0074722 A1 | 4/2007 | Giroux et al. |
| 2007/0114279 A1 | 5/2007 | Lessing et al. |
| 2007/0150382 A1 | 6/2007 | Danilewitz |
| 2007/0187475 A1 | 8/2007 | MacLeod |
| 2007/0188306 A1 | 8/2007 | Tethrake et al. |
| 2007/0200702 A1 | 8/2007 | Chung |
| 2007/0213659 A1 | 9/2007 | Trovato et al. |
| 2007/0213684 A1 | 9/2007 | Hickle et al. |
| 2007/0229268 A1 | 10/2007 | Swan et al. |
| 2008/0004908 A1 | 1/2008 | Oh et al. |
| 2008/0012687 A1 | 1/2008 | Rubinstein |
| 2008/0045930 A1 | 2/2008 | Makin et al. |
| 2008/0046295 A1 | 2/2008 | Albrecht |
| 2008/0094214 A1 | 4/2008 | Azevedo et al. |
| 2008/0122878 A1 | 5/2008 | Keefe et al. |
| 2008/0128482 A1 | 6/2008 | Chen et al. |
| 2008/0129496 A1 | 6/2008 | Koblasz |
| 2008/0150722 A1 | 6/2008 | Jackson |
| 2008/0172253 A1 | 7/2008 | Chung et al. |
| 2008/0191013 A1 | 8/2008 | Liberatore |
| 2008/0218307 A1 | 9/2008 | Schoettle |
| 2008/0243088 A1 | 10/2008 | Evans |
| 2008/0270178 A1 | 10/2008 | McRae et al. |
| 2008/0296373 A1 | 12/2008 | Smood et al. |
| 2008/0297356 A1 | 12/2008 | Oberle |
| 2008/0306772 A1 | 12/2008 | Shahrokh |
| 2008/0316045 A1 | 12/2008 | Sriharto et al. |
| 2009/0002173 A1 | 1/2009 | Bergsten et al. |
| 2009/0020442 A1 | 1/2009 | Dietrich et al. |
| 2009/0058653 A1 | 3/2009 | Geissler et al. |
| 2009/0144087 A1 | 6/2009 | Kelsch et al. |
| 2009/0153290 A1 | 6/2009 | Bierach |
| 2009/0164042 A1 | 6/2009 | Handfield et al. |
| 2009/0194987 A1 | 8/2009 | Christie et al. |
| 2009/0231138 A1 | 9/2009 | Cheung et al. |
| 2009/0267740 A1 | 10/2009 | Pizzuto et al. |
| 2009/0267772 A1 | 10/2009 | Dehnadi |
| 2009/0277815 A1 | 11/2009 | Kohl |
| 2009/0294521 A1 | 12/2009 | De La Huerga |
| 2010/0022953 A1 | 1/2010 | Bochenko et al. |
| 2010/0022987 A1 | 1/2010 | Bochenko |
| 2010/0036310 A1 | 2/2010 | Hillman |
| 2010/0036678 A1 | 2/2010 | Bray |
| 2010/0036755 A1 | 2/2010 | Saghbini |
| 2010/0042439 A1 | 2/2010 | Martinez et al. |
| 2010/0079337 A1 | 4/2010 | Hsu et al. |
| 2010/0098425 A1 | 4/2010 | Kewitsch |
| 2010/0108761 A1 | 5/2010 | Nycz et al. |
| 2010/0114951 A1 | 5/2010 | Bauman et al. |
| 2010/0185458 A1 | 7/2010 | Calderwood et al. |
| 2010/0204659 A1 | 8/2010 | Bochenko |
| 2010/0217621 A1 | 8/2010 | Schoenberg et al. |
| 2010/0219097 A1 | 9/2010 | Ramasubramanian et al. |
| 2010/0238039 A1 | 9/2010 | Tethrake et al. |
| 2010/0268548 A1 | 10/2010 | Garrett et al. |
| 2010/0275625 A1 | 11/2010 | Lowenstein |
| 2010/0299158 A1 | 11/2010 | Siegel |
| 2010/0328474 A1 | 12/2010 | Hsieh |
| 2010/0332246 A1 | 12/2010 | Fedorko et al. |
| 2011/0006879 A1 | 1/2011 | Bartos |
| 2011/0063091 A1 | 3/2011 | Kang |
| 2011/0068922 A1 | 3/2011 | Ross |
| 2011/0093279 A1 | 4/2011 | Davison et al. |
| 2011/0115612 A1 | 5/2011 | Kulinets et al. |
| 2011/0125315 A1 | 5/2011 | Handfield et al. |
| 2011/0131056 A1 | 6/2011 | Chudy et al. |
| 2011/0139871 A1 | 6/2011 | Yturralde et al. |
| 2011/0161112 A1 | 6/2011 | Keefe et al. |
| 2011/0163871 A1 | 7/2011 | Einav et al. |
| 2011/0166878 A1 | 7/2011 | Louie et al. |
| 2011/0184751 A1 | 7/2011 | Holmes |
| 2011/0225100 A1 | 9/2011 | Sangal et al. |
| 2011/0227722 A1 | 9/2011 | Salvat, Jr. |
| 2011/0240729 A1 | 10/2011 | Schuck |
| 2011/0257991 A1 | 10/2011 | Shukla |
| 2011/0270441 A1 | 11/2011 | Handfield et al. |
| 2011/0291809 A1 | 12/2011 | Niemiec et al. |
| 2011/0301446 A1 | 12/2011 | Kamen |
| 2011/0313395 A1 | 12/2011 | Krulevitch et al. |
| 2012/0037266 A1 | 2/2012 | Bochenko |
| 2012/0041778 A1 | 2/2012 | Kraft |
| 2012/0044054 A1 | 2/2012 | Hussain et al. |
| 2012/0061463 A1 | 3/2012 | Burke |
| 2012/0089411 A1 | 4/2012 | Srnka et al. |
| 2012/0089418 A1 | 4/2012 | Kamath et al. |
| 2012/0116798 A1 | 5/2012 | Heath et al. |
| 2012/0125994 A1 | 5/2012 | Heath et al. |
| 2012/0173440 A1 | 7/2012 | Becker et al. |
| 2012/0177256 A1 | 7/2012 | Keefe et al. |
| 2012/0179132 A1 | 7/2012 | Valk et al. |
| 2012/0185951 A1 | 7/2012 | Bauman et al. |
| 2012/0209619 A1 | 8/2012 | Knotts et al. |
| 2012/0240067 A1 | 9/2012 | Bauman et al. |
| 2012/0273087 A1 | 11/2012 | Einy et al. |
| 2012/0278096 A1 | 11/2012 | Holness |
| 2012/0278228 A1 | 11/2012 | Rubinstein |
| 2012/0323208 A1 | 12/2012 | Bochenko et al. |
| 2012/0325330 A1 | 12/2012 | Prince et al. |
| 2013/0018356 A1 | 1/2013 | Prince et al. |
| 2013/0035950 A1 | 2/2013 | MacDonald et al. |
| 2013/0038452 A1 | 2/2013 | Sawyer |
| 2013/0041784 A1 | 2/2013 | Danilewitz |
| 2013/0092727 A1 | 4/2013 | Edwards et al. |
| 2013/0105568 A1 | 5/2013 | Jablonski et al. |
| 2013/0151005 A1 | 6/2013 | Gerold et al. |
| 2013/0191149 A1 | 7/2013 | Kolberg et al. |
| 2013/0221082 A1 | 8/2013 | Botten |

(56) References Cited

U.S. PATENT DOCUMENTS

| | | | |
|---|---|---|---|
| 2013/0221087 | A1 | 8/2013 | Keefe et al. |
| 2013/0225945 | A1 | 8/2013 | Prince et al. |
| 2013/0327822 | A1 | 12/2013 | Keefe et al. |
| 2014/0060729 | A1 | 3/2014 | Srnka et al. |
| 2014/0066880 | A1 | 3/2014 | Prince et al. |
| 2014/0117081 | A1 | 5/2014 | Jablonski et al. |
| 2014/0136229 | A1 | 5/2014 | Levine et al. |
| 2014/0142975 | A1 | 5/2014 | Keefe et al. |
| 2014/0184390 | A1 | 7/2014 | Elizondo, II |
| 2014/0184391 | A1 | 7/2014 | Elizondo, II |
| 2014/0197954 | A1 | 7/2014 | Caputo et al. |
| 2014/0210596 | A1 | 7/2014 | Hussain et al. |
| 2014/0262919 | A1 | 9/2014 | Hussain et al. |
| 2014/0263614 | A1 | 9/2014 | Keefe et al. |
| 2014/0276213 | A1 | 9/2014 | Bochenko |
| 2014/0282197 | A1 | 9/2014 | Keefe et al. |
| 2014/0291397 | A1 | 10/2014 | Caputo et al. |
| 2014/0367080 | A1 | 12/2014 | Hussain et al. |
| 2014/0372145 | A1 | 12/2014 | MacDonald et al. |
| 2015/0058182 | A1 | 2/2015 | Kress-Spatz et al. |
| 2015/0161558 | A1 | 6/2015 | Gitchell et al. |
| 2015/0235005 | A1 | 8/2015 | MacDonald et al. |

FOREIGN PATENT DOCUMENTS

| | | |
|---|---|---|
| CN | 102791310 B | 12/2014 |
| EP | 2 496 283 | 9/2012 |
| IN | 2012/04914 P4 | 10/2013 |
| WO | WO 02/095675 | 11/2002 |
| WO | WO 03/071943 | 9/2003 |
| WO | WO 2006026246 | 3/2006 |
| WO | WO 2006/135830 | 12/2006 |
| WO | WO 2010/074781 | 7/2010 |
| WO | WO 2011/056888 | 9/2011 |
| WO | WO 2011/115676 | 9/2011 |
| WO | WO 2011/150013 | 12/2011 |
| WO | WO 2013/082423 | 6/2013 |
| WO | WO 2013/116873 | 8/2013 |
| WO | WO 2013/134256 | 9/2013 |
| WO | WO 2014/159928 | 10/2014 |
| WO | WO 2014/189834 | 11/2014 |
| WO | WO 2015/026387 | 2/2015 |

OTHER PUBLICATIONS

U.S. Appl. No. 14/126,419, filed Dec. 14, 2013, including its ongoing prosecution history, including without limitation Office Actions, Amendments, Remarks, and any other potentially relevant documents, Kress-Spatz, et al.
Curtin, John, et al., Making the 'MOST' out of RFID: a research agenda for the study of the adoption, usage and impact of RFID,: Information Technology Management (Apr. 2007) 8 pp. 87-110.
Crash Cart Inventory Checklist, Outpatient Surgery Magazine, Oct. 2004, "Outpatient Surgery" in 1 page, available at: http://www.outpatientsurgery.net/resources/forms/2004/pdf/OutpatientSurgeryMagazine_0410_crashCart.pdf.
Gonzalez, Stephanie, "Health Maintenance System (HMS) Hardware Research, Design, and Collaboration," NASA USRP—Internship Final Report (2010), pp. 1-20.
Harrop, Peter, et al., "RFID for Healthcare and Pharmaceuticals, 2008-2018," Securing Pharma, May 2008, pp. 1-12.
Lai, Chun-Liang, et al., "Enhancing Medication Safety and Reduce Adverse Drug Events on Inpatient Medication Administration using RFID," WSEAS Transactions on Communications, Issue 10, vol. 7, Oct. 2008, pp. 1045-1054.
Lampe, Matthias, et al., "The smart box application model," Advances in pervasive computing, 2004, pp. 1-6.
Medical Packaging Inc. Announces Clear Stem Flag Label System for Ampoules, Vials, and Syringes in 1 page (Feb. 1, 2006) available at: http://www.medpak.com/v1/news/20060201_CSFLAG.pdf.
O'Driscoll, C., et al, "RFID: An Ideal Technology for Ubiquitous Computing?," Dublin Institute of Technology School of Electronic and Communications Conference Papers, Jan. 1, 2008, pp. 1-17.
Tzeng, Shiou-Fen, et al., "Evaluating the business value of RFID: Evidence from five case studies," International Journal of Production Economics 112 (2008) pp. 601-813.
Wang et al., "Applying RFID Technology to Develop a Distant Medical Care Service Platform," International Journal of Electronic Business Management, (2010) vol. 8, No. 2, pp. 161-170.
U.S. Appl. No. 14/603,730, filed Jan. 23, 2015, including its ongoing prosecution history, including without limitation Office Actions, Amendments, Remarks, and any other potentially relevant documents, MacDonald et al.
U.S. Appl. No. 14/603,828, filed Jan. 23, 2015, including its ongoing prosecution history, including without limitation Office Actions, Amendments, Remarks, and any other potentially relevant documents, MacDonald et al.
U.S. Appl. No. 14/603,962, filed Jan. 23, 2015, including its ongoing prosecution history, including without limitation Office Actions, Amendments, Remarks, and any other potentially relevant documents, MacDonald et al.
U.S. Appl. No. 14/563,732, filed Dec. 8, 2014, including its ongoing prosecution history, including without limitation Office Actions, Amendments, Remarks, and any other potentially relevant documents, Gitchell et al.
U.S. Appl. No. 14/469,524, filed Aug. 26, 2014, including its ongoing prosecution history, including without limitation Office Actions, Amendments, Remarks, and any other potentially relevant documents, MacDonald et al.
Belson, D., "Storage, Distribution, and Dispensing of Medical Supplies," CREATE Interim Report Under FEMA Grant EMW-2004-GR-0112, Apr. 21, 2005, pp. 1-36.
Houliston, Bryan, "Integrating RFID Technology into a Drug Administration System," Bulletin of Applied Computing and Information Technology, vol. 3, No. 1, May 2005, pp. 8. Retrieved Sep. 26, 2013 from http://citrenz.ac.nz/bacit/0301/2005Houliston_RFID.htm.
Jorgensen et al., "Executable Use Cases: Requirements for a Pervasive Health Care System," IEEE Software, Mar./Apr. 2004, pp. 34-41.
"McKesson's Announces New Touch-Screen Driven Medication Dispensing Solution", Business Wire, Jun. 15, 2009, p. 2, Available at: http://www.businesswire.com/news/home/20090615005349/en/McKesson-Announces-Touch-Screen-Driven-Medication-Dispensing-Solution#.VR7quPnF_10.
Pappu, Ph.D. et al., "RFiD in Hospitals: Issues and Solutions" Consortium for the Accelerated Deployment of RFID in Distribution, Sep. 2004, pp. 1-12.
Co-pending U.S. Appl. No. 14/126,419, filed Dec. 14, 2013.
U.S. Pat. No. 9,037,479, including its prosecution history, including without limitation: Office Actions, Amendments, Remarks, and any other potentially relevant documents.
U.S. Pat. No. 9,058,412, including its prosecution history including without limitation: Office Actions, Amendments, Remarks, and any other potentially relevant documents.
U.S. Pat. No. 9,058,413, including its prosecution history, including without limitation: Office Actions, Amendments, Remarks, and any other potentially relevant documents.
U.S. Appl. No. 14/818,101, filed Aug. 4, 2015, including its ongoing prosecution history, including without limitation Office Actions, Amendments, Remarks, and any other potentially relevant documents, MacDonald et al.
U.S. Appl. No. 14/818,113, filed Aug. 4, 2015, including its ongoing prosecution history, including without limitation Office Actions, Amendments, Remarks, and any other potentially relevant documents, MacDonald et al.
U.S. Appl. No. 14/876,533, filed Oct. 6, 2015, including its ongoing prosecution history, including without limitation Office Actions, Amendments, Remarks, and any other potentially relevant documents, Gitchell et al.
O'Connor, To Keep Drugs from Expiring, Hospital Tests Intelliguard System, RFID Journal, Jan. 12, 2011, 3 pgs.

\* cited by examiner

Add Formulary Item to Segment

400

NDC: 0409-7241-61

Manufacturer: Hospira

Name: Epinephrine Injection USP (1:1000)

Strength: 1 mg/mL

Package: 2 mL syringe

Add to Segment: Epinephrine ▶

Add to Fill Option: ○ Preferred Fill Option
○ Alternative Fill Option

Cancel

Save

FIG.4

Edit Fill Option

Quantity: 2   Billing Code: 10468

Add Items

[ epi  ⊗ ]

| NDC | Manufacturer | Name | Strength | Package | |
|---|---|---|---|---|---|
| 0409-7241-61 | Hospira | Epinephrine Injection USP (1:1000) | 1 mg/mL | 2 mL syringe | + Add |
| 0409-3375-04 | Med Tools | Norepinephrine Bitartrate | 1 mg/mL | 4 mL syringe | + Add |
| 42023-101-10 | Acme Inc | EPINEPHrine 1:1000 | 1 mg/mL | 30 mL vial | + Add In another fill option in this segment |
| 0409-7241-01 | Hospira | EPINEPHrine HCl | 1 mg/mL | 25 mL ampule | + Add In this fill option |
| 49502-500-01 | Acme Inc | EpiPen | 0.3 mg | 0.3 mL auto-injector | + Add In another fill option in this kit |

Items in Fill Option (3)

| NDC | Manufacturer | Name | Strength | Package | |
|---|---|---|---|---|---|
| 0409-7241-01 | Hospira | EPINEPHrine HCl | 1 mg/mL | 25 mL ampule | × Remove |
| 0409-7241-81 | Hospira | Epinephrine USP (1:1000) | 1 mg/mL | 25 mL vial | × Remove |
| 5171l3005 | Unknown | Epinephrine | | 25 mL vial | × Remove |

[ Cancel ]   [ Done ]

| Edit Segment | ⓘ |
|---|---|

General OR Kit

Segment Name: | Epinephrine inj 1 mg/mL |

Fill Options
If the items in your kit match any one of the fill options below, the segment will be considered complete; otherwise, Kit Check will show which items are missing or extra based on the preferred template.

[ + Add Fill Option ]

Preferred Fill Option — Edit

Quantity 3    Billing Code 10468    Created May 1, 2014

| NDC | Manufacturer | Name | Strength | Package |
|---|---|---|---|---|
| 0409-7241-01 | Hospira | EPINEPHrine HCl | 1 mg/mL | 25 mL ampule |
| 999-01-0296 | Hospital | Epinephrine | | 25 mL vial |

Alternative Fill Option — Set as Preferred    Delete    Edit

Quantity 2    Billing Code 10465    Created July 31, 2013

| NDC | Manufacturer | Name | Strength | Package |
|---|---|---|---|---|
| 0409-7241-01 | Hospira | EPINEPHrine HCl | 1 mg/mL | 25 mL ampule |
| 0409-7241-81 | Hospira | Epinephrine USp (1;1000) | 1 mg/mL | 25 mL vial |
| 517113005 | Unknown | Epinephrine | | 25 mL vial |

[ Delete Segment ]                              [ Cancel ]   [ Save ]

FIG.6

Item Summary by Segment

| Segment | Item Count | Earliest Expiration Date | Used |
|---|---|---|---|
| Albuterol Sulfate HFA 6.7 g | 2  Extra: 1 | | Nov 30, 2015 |
| Ampicillin 1 g<br>▫▫ Matched a non-preferred fill option | 3  Extra: 1 | | Jul 31, 2014<br>in 36 days |
| Ampicillin/Sulbactam 1.5 gm | 2 | | Mar 31, 2015 |
| Artificial Tear Eye Ointment | 4  Extra: 1 | | Jan 31, 2017 |
| Atropine 0.4 mg/mL | 2  Extra: 1 | | Jun 30, 2015 |

KITCHECK | SCAN | Inventory | Tags | Reports | KitCheck TechTeam

Manage Kit Masters

Kit Master: Anesthesia C-Section Tray ▼

Anesthesia C-Section Tray Segments | Rename Kit Master | + New Segment

| Segment ▲ | Quantity | Billing Code |
|---|---|---|
| This segment has multiple fill options | | |
| ☐☐ Diphenhydramine 50 mg/ml vial  (Show alternatives) | 1 | 10920 |
| ☐☐ Ephedrine 50 mg/ml ampule  (Hide alternatives) | 1 | 10975 |
| ☐☐ Epinephrine 1:10,000 syringe | 1 | 10980 |
| (Preferred Fill Option) | 2 | 10981 |
| (Alternative Fill Option) | 1 | 10985 |
| Esmolol 100 mg/10 ml vial | 5 | 14335 |
| Fentanyl 50 mcg/ml 2 ml | 1 | 11009 |
| Glycopyrrolate 0.2 mg/ml 5 ml vial  (Show alternatives) | — | — |
| ☐☐ Hydralazine 20 mg/ml vial | | |

| Scan Summary | Scan Details |

All Items by Segment

| Segment ▼ | Manufacturer | Item / NDC / Lot Number | Expiration |
|---|---|---|---|
| Amiodarone inj 150 mg/3 mL<br>▢▢ Matched a non-preferred fill option | APP PHARMACEUTICAL | Amiodarone HCl 150MG/3ML 3ML<br>NDC: 63323-616-03<br>Lot: 6006935 | Jan 31, 2015 |
| | BIONICHE PHARMA GROUP | Amiodarone HCl 150MG/3ML 3ML<br>NDC: 67457-153-03<br>Lot: 130525 | Oct 31, 2014 |
| | BIONICHE PHARMA GROUP | Amiodarone HCl 150MG/3ML 3ML<br>NDC: 67457-153-03<br>Lot: 130525 | Oct 31, 2014 |
| | BIONICHE PHARMA GROUP | Amiodarone HCl 150MG/3ML 3ML<br>NDC: 67457-153-03<br>Lot: 130525 | Oct 31, 2014 |

Items Expiring Soon

| Item ▶ | Manufacturer | NDC | Lot Num | Expiration |
|---|---|---|---|---|
| Naloxone HCl 0.4 mg/mL<br>EPC: D8ED | HOSPIRA | 0409-1215-01 | 20175EV | Aug 1, 2014 |

[Print Billing Sheet]

Missing Items

|  | Expected | Actual | Shortage |
|---|---|---|---|
| [This segment has multiple fill options]<br>⊞ Epinephrine inj 1 mg/mL | 3 | 2 | 1 |
| ⊞ Naloxone HCl 0.4 mg/mL | 2 | 1 | 1 |

Extra Items

| Segment ▲ | Expected | Actual | Surplus |
|---|---|---|---|
| Saline Water | 10 | 11 | 1 |

Wrong Items for this Kit

| Item ▶ | Manufacturer | NDC | Lot Num | Expiration |  |
|---|---|---|---|---|---|
| Dextrose 50%<br>EPC: 9753 | INTRNTL MEDICATION SYSTEM | 76329-3301-1 | bd043d3 | Mar 31, 2015 | + Add Formulary<br>Item to Segment |

| Segment | Permissible Items | Quantity |
|---|---|---|
| Medicine Bottle 1 | Product A<br>Product B | 1 |
| Medicine Vial 2 | Product C<br>Product D<br>Product E | 3 |
| Medicine Bag 3 | Product F | 2 |
| Solution Bottle 4 | Product G<br>Product H | 3 |
| Etc. | . . . | . . . |

FIG. 11B

All Items by Segment 105

| Segment | Brand | Item/NDC/Lot | Strength | Expiration |
|---|---|---|---|---|
| Adenosine Vial | | Adenosine Injection NDC: 1001906302 Lot: 916136 | 6 mg/2 mL | Feb 28, 2013 |
| | Adenosine Injection | Adenosine Injection NDC: 1001906302 Lot: 916136 | 6 mg/2 mL | Feb 28, 2013 |
| | Adenosine Injection | Adenosine Injection NDC: 1001906302 Lot: 916136 | 6 mg/2 mL | Nov 30, 2013 |
| Albuterol IPPB Sol. | Ipratropium Bromide And Albuterol Sulfate | Ipratropium Bromide and Albuterol Sulfate NDC: 0487-0201-60 Lot: 76AN1 | 3; .5mg/3mL; mg/3mL | Dec 31, 2017 |
| | Ipratropium Bromide And Albuterol Sulfate | Ipratropium Bromide and Albuterol Sulfate NDC: 0487-0201-60 Lot: 76AN1 | 3; .5mg/3mL; mg/3mL | Dec 31, 2017 |
| Albuterol MDI | VENTOLIN | VENTOLIN NDC: 0173-0682-54 Lot: 1ZP6940 | 108 ug/1 | Nov 30, 2012 |
| Amiodarone Vial | Amiodarone Hydrochloride | Amiodarone Hydrochloride NDC: 67457-153-03 Lot: 101210 | 50 mg/mL | Oct 31, 2012 |
| | Amiodarone Hydrochloride | Amiodarone Hydrochloride NDC: 67457-153-03 Lot: 101210 | 50 mg/mL | Oct 31, 2012 |
| Atropine Bristojet | | Atropine NDC: 0548-3339-00 Lot: 1 | 1 mg/10 mL | Feb 28, 2014 |
| | | Atropine NDC: 0548-3339-00 Lot: 1 | 1 mg/10 mL | Feb 28, 2014 |
| Calcium Chloride Bristoject | | Calcium Chloride NDC: 0548-3304-00 Lot: BA00219 | 100 mg.mL | Aug 30, 2012 |
| | | Calcium Chloride | 100 mg.mL | Aug 30, 2012 |

FIG. 11C

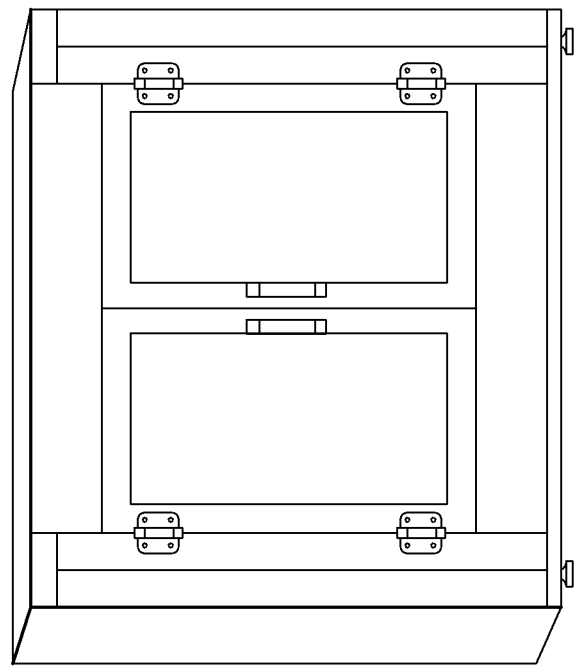
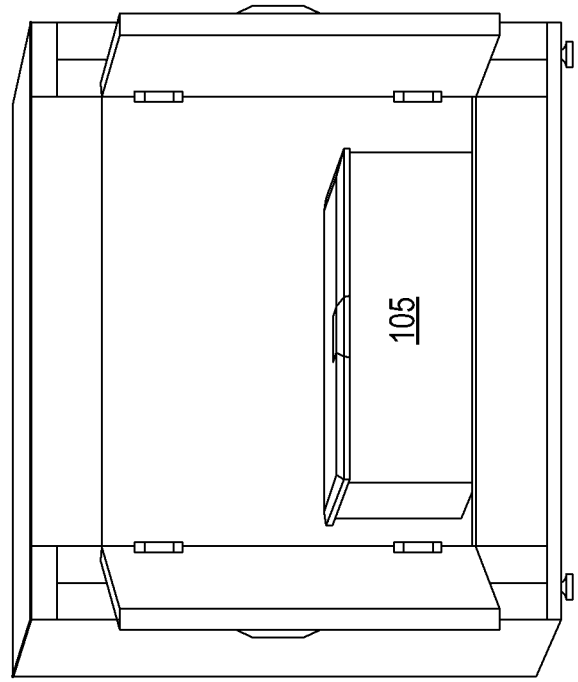
FIG. 12B

905 —

⚡ Scan  ◆ Kits  ▦ Reports  🏷 Print Tags

1001

Pediatric Emergency Drug Tray | KitCheck-3
Drug Tray (3)

1005 —

| 51 Total | | |
|---|---|---|
| 0 Extra | 1 Missing | |
| | 0 Expired | 2 Expiring |

1010 —

▦ Procainamide Hydrochloride on October 1, 2012

1015 — Last Scan   September 28, 2012   Scan History | Details

Items Expiring Soon

1020 —

| Manufacturer | Item | Size | Item Num (NDC) | Lot Num | Expiration |
|---|---|---|---|---|---|
| Hospira, Inc. | Procainamide Hydrochloride | 500 mg/mL | 0409-1903-01 | 1 | October 1, 2012 |
| Hospira, Inc. | Procainamide Hydrochloride | 500 mg/mL | 0409-1903-01 | 1 | October 1, 2012 |

Missing Items

1025 —

| Shortage | Item | Expected | Actual |
|---|---|---|---|
| 1 | Magnesium Sulfate Vial | 2 | 1 |

| 905 — | Demo Kit | | Scan | Kits | Reports | Print Tags | |
|---|---|---|---|---|---|---|---|
| | Tray (9) | | | | | | Check Out |

| 26 Total | 0 Extra | 1 Missing | | | Central Pharmacy | |
|---|---|---|---|---|---|---|

1105 —

1110 — | 1 Expired | 1 Expiring | | Protopic on September 28, 2012 |

1115 — Last Scan  October 1, 2012  ▶ Show Scan History | Details

Expired Items

1120 —

| Manufacturer | Item | Size | Lot Num | Expiration |
|---|---|---|---|---|
| Astellas | Protopic | 39487279 | 28841 | September 28, 2012 |

Items Expiring Soon

1125 —

| Manufacturer | Item | Size | Item Num | Lot Num | Expiration |
|---|---|---|---|---|---|
| Alcon | Pataday Olopatadine Hydrochloride Opthalmic s | 1 Box | 650277224 | 174872F-1 | October 1,2012 |

Extra Items

1130 —

| Item | Expected | Actual | Surplus |
|---|---|---|---|
| Olopatadine Hydrochloride Opthalmic solution | 2 | 3 | 1 |
| Tacrolimus ointment 0.1% | 1 | 2 | 1 |

Select a Report [Kits that needs rework ▼]      1300A

☑ Surplus     ☑ Shortage     ☑ Expired     ☑ Expiring

☐ All Segments

Kits that needs rework

[Expand All] [Collapse All]

| Demo Kit | | Qty Expected | Item Num (NDC) | Lot Num | Expiration |
|---|---|---|---|---|---|
| Fluticasone Propionate Nasal Spray 50 Mcg | Shortage:1 | 2 | | | January 1, 2012 |
| Gentamicin Sulfate USP 0.3% | | 1 | | | November 3, 2012 ⚠ |
| Bandage Kit – Gauge and overpacked | | Qty Expected | Item Num (NDC) | Lot Num | Expiration |
| Large Bandages | Shortage:3 | 3 | | | |
| Medium Bandages | Shortage:3 | 3 | | | |
| Round Bandages | Shortage:3 | 3 | | | |

1305A — top section; 1310A — table section

FIG.22A

Select a Report: | Kits containing a specific item or lot number ▶ |

Manufacturer Name

Item Name

Item Number (NDC)

Lot Number | PAA32 |

Kits containing a specific item or lot number

| Demo Kit | | Item Num (NDC) | Lot Num | Expiration |
|---|---|---|---|---|
| Teva | ProAir HFA | 1 Box | 5931057920 | PAA32A | January 1, 2012 |

FIG. 22B

MANAGEMENT OF PHARMACY KITS USING MULTIPLE ACCEPTANCE CRITERIA FOR PHARMACY KIT SEGMENTS

CROSS-REFERENCE TO RELATED APPLICATIONS

This application is a continuation-in-part of U.S. patent application Ser. No. 13/554,342 filed Jul. 20, 2012, published as U.S. Patent Application Publication No. 2013/0035950, the subject matter of which is hereby incorporated by reference. U.S. patent application Ser. No. 13/554,342 claims priority benefit to U.S. Provisional Application No. 61/514,231, filed Aug. 2, 2011. This application also claims priority to U.S. Provisional Application No. 62/021,927 filed on Jul. 8, 2014, the subject matter of which is hereby incorporated by reference.

BACKGROUND

Hospital pharmacies often manage groups of medical items in the form of pharmacy kits. A pharmacy kit can be used, for instance, to provide a group of items for a specific medical procedure, a particular physician, or a designated location of a hospital. As an example, a pharmacy kit can be used to aggregate and transport a collection of medicines for treating a patient with a specific type of stroke, heart condition, or other ailment.

A pharmacy kit (or "kit") typically comprises a group of items specified by a template. For example, the template may specify that the kit requires three vials of adenosine, two containers of albuterol solution, two vials of amiodarone, and so on. The template may also specify ways in which individual items may be satisfied. For example, it may specify that the vials of adenosine may be satisfied by certain product brands. Pharmacy kits are usually stocked by a hospital pharmacy, but they may be stocked by another entity, such as an outsourced kit stocking company.

A kit is typically created by receiving specified items in a pharmacy, manually recording (e.g., on paper and/or electronic records) their product identifiers (e.g., National Drug Code (NDC) or Universal Product Code (UPC)), lot numbers, and expiration dates, and then loading the items into a container, such as a box, tray, or canister. During the kit's lifetime, it may be updated periodically to replace expired or consumed items. These updates are typically performed by inspecting the kit, comparing it to a corresponding template, modifying kit contents as required, and then manually recording any changes.

One challenge that may complicate the management of pharmacy kits is the rise of medication shortages across the country. From normal saline to propofol, any particular item can go into shortage almost inexplicably. As a result, hospitals are often forced to use different sizes or concentrations than what they normally stock or administer. This, unfortunately, may prevent accurate inventory monitoring and disrupt current processes of kit management.

Due to the above and other shortcomings of conventional approaches, there is a general need for improved techniques and technologies for managing pharmacy kits in the face of inventory shortages.

SUMMARY

In one embodiment of the inventive concept, a method of managing a pharmacy kit comprises determining whether a kit stocking contingency has occurred with respect to a segment of the pharmacy kit, as a consequence of determining that the kit stocking contingency has not occurred, determining whether the segment has been satisfactorily stocked according to a first acceptance criterion, and as a consequence of determining that the kit stocking contingency has occurred, determining whether the segment has been satisfactorily stocked according to a second acceptance criterion different from the first acceptance criterion.

In another embodiment of the inventive concept, a method of managing a pharmacy kit using an electronic information processing system comprises defining, in the electronic information processing system, multiple rules for determining whether a segment of a pharmacy kit is satisfactorily stocked, selecting, by the electronic information processing system, at least one rule among the multiple rules according to a kit stocking contingency, and prompting, by the electronic information processing system, a user to stock the segment of the pharmacy kit according to the selected at least one rule.

BRIEF DESCRIPTION OF THE DRAWINGS

The drawings illustrate selected embodiments of the inventive concept. In the drawings, like reference labels denote like features.

FIG. 4 shows an interface for adding a fill option to a segment of a pharmacy kit according to an embodiment of the inventive concept.

FIG. 5 shows an interface for modifying fill options for a segment of a pharmacy kit according to an embodiment of the inventive concept.

FIG. 6 shows an interface for adding, removing, or modifying fill options for a segment of a pharmacy kit according to an embodiment of the inventive concept.

FIG. 7 shows an interface indicating that an alternate fill option has been used to stock a segment of a pharmacy kit, according to an embodiment of the inventive concept.

FIG. 8 shows an interface with icons indicating that alternate fill options exist for certain segments of a pharmacy kit, according to an embodiment of the inventive concept.

FIG. 9 shows an interface identifying the contents of a segment of a pharmacy kit, together with an indication that alternate fill options were used to stock the segment, according to an embodiment of the inventive concept.

FIG. 10 shows an interface displaying exceptions in a kit with an icon to indicate that missing items can be restocked to match one of multiple rules for a segment, according to an embodiment of the inventive concept.

FIGS. 11A, 11B, and 11C are diagrams illustrating a pharmacy kit according to an embodiment of the inventive concept.

FIGS. 12A and 12B are diagrams of a read station in the system of FIG. 1 according to an embodiment of the inventive concept.

FIG. 19 shows a report generated for a pharmacy kit using the system of FIG. 1 according to an embodiment of the inventive concept.

FIG. 20 shows another report generated for a pharmacy kit using the system of FIG. 1 according to an embodiment of the inventive concept.

FIGS. 22A and 22B show interfaces used to generate and view reports regarding pharmacy kits according to an embodiment of the inventive concept.

DETAILED DESCRIPTION

Figure 1:
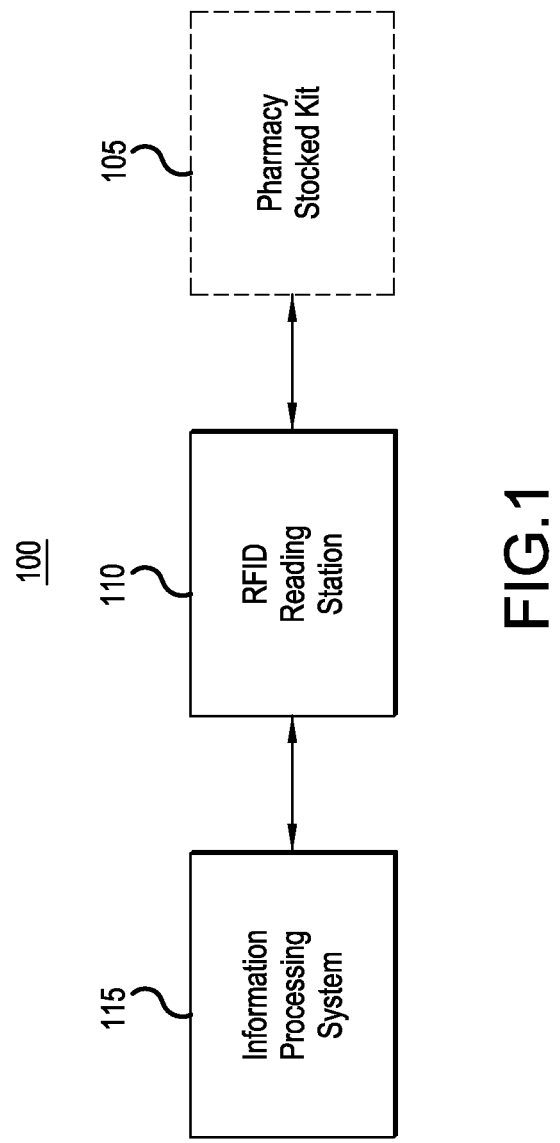
FIG. 1 is a block diagram of a system for managing pharmacy kits according to an embodiment of the inventive concept.

Embodiments of the inventive concept are described below with reference to the accompanying drawings. These embodiments are presented as teaching examples and are not to be construed as limiting the scope of the inventive concept.

The described embodiments relate generally to the management of pharmacy kits. Certain details of pharmacy kits and related methods of management are described in U.S. patent application Ser. No. 13/554,342 filed Jul. 20, 2012, published as U.S. Patent Application Publication No. 2013/0035950, and U.S. patent application Ser. No. 14/126,419 filed Dec. 14, 2013, the respective disclosures of which are hereby incorporated by reference.

In certain embodiments, a kit management system uses RFID technology to label and track the contents of a kit. The use of RFID technology can allow a pharmacy to accurately and efficiently determine whether items in the kit are consumed, missing, expired, or near expiration. These determinations can be used thereafter to verify and update the kit contents, track item usage patterns, generate patient billing information based on item consumption, and so on.

In certain embodiments, a hospital pharmacy begins by tagging items upon bulk receipt in the hospital, or when a kit is stocked. Alternatively, items may arrive at a hospital pre-tagged. One way to tag the items is by scanning bar codes present on most items used in a kit, printing RFID tags based on the scanned bar codes, and then applying the RFID tags to the items. The scanned bar codes typically provide item information such as product identifiers (e.g., NDC or UPC), lot numbers, and expiration dates. This information can be associated with the RFID tags in a computer database to allow subsequent identification and processing by RFID technology. In some embodiments, the RFID tags can be generated automatically when scanning the bar codes, e.g., through the use of an RFID tag printer operatively connected to a bar code scanning machine. Alternatively, the RFID tags may be non-printed tags.

A kit is typically built by placing tagged items in a container such as a box, tray, or canister, and optionally labeling the kit with an RFID tag having information such as a kit identifier, kit type, intended user, or location, for example. These steps are generally performed by a pharmacist or other competent medical professional.

Once a kit is built, its contents are verified by placing it in an RFID reading station, which reads all RFID tags within its sensing range to identify the kit type and any items present. In some embodiments, the RFID reading station includes an enclosure such as a metal box to allow scanning of the kit exclusive of other RFID devices that may be in the surrounding environment. Alternatively, the RFID reading station may omit such an enclosure, for instance, by performing reading in an open area such as table, or using a handheld RFID reader. If the kit has an RFID tag, the kit type can be determined from the tag. Otherwise, it may be inferred from the items present. Items are typically identified by recognizing their RFID tags and then accessing stored information that maps the RFID tags to specific item information.

The stored information may reside on electronic equipment located at the RFID reader station or a remote location such as a remote server, a personal computer (PC), a mobile device, etc. In addition to basic kit and item information, the electronic equipment may also store metadata related to kit processes, such as who built or rebuilt a kit, what items were replaced if the kit was restocked, when the items were inserted in the kit, when verification and update procedures were last performed or will next be performed, and so on.

After the kit and item information are determined by the kit management system, they are analyzed automatically with reference to one or more templates. For instance, a kit template may be located based on the kit type, and then the identified items may be compared with the kit template to determine whether any items are missing or require replacement based on use or expiration. Additionally, the information processing system may analyze item information to determine whether any items are expired or will soon expire. The kit can then be updated based on these analyses.

Kit templates are typically stored in a database within or associated with the information processing system. However, they can alternatively be stored within a memory associated within the RFID reading station or RFID reader, or they can be stored in a separate system accessible by the information processing system.

In general, expiration of an item may occur based on a fixed or variable timeframe. For example, some items may expire at a fixed date indicated by the manufacturer, while other items may expire after a certain amount of time out of the refrigerator, e.g., time of removal+X days. Whether the timeframe is fixed or variable can be indicated in the template at a master level for a particular item, or at a segment level for a segment including the item.

The automatic processing provided by RFID technology and associated electronic equipment allows kit management to be performed with greater efficiency and accuracy compared with conventional approaches. For instance, in some embodiments, kit contents and expiration dates can be validated in 15 seconds or less. Moreover, kit deficiencies can be reported to a pharmacist automatically, allowing them to be addressed in an efficient manner. This reporting can be accomplished, for instance, by an automatically generated charge sheet showing kit contents and expirations.

Once a kit is built and verified, it is ready to be sealed and deployed for use in the hospital. When a kit is used, the seal is broken and items may be removed or consumed. Accordingly, the kit may be subsequently returned to the RFID reading station for additional verification, monitoring, and updates. These additional procedures can be used, for example, to determine whether any items in the kit are missing (e.g., due to use), and whether any items are erroneously present in the kit. This information can then be used to generate a report indicating the status and any necessary updates for the kit, or for other purposes such as patient billing or supply ordering. Once the relevant information is collected, the kit can be rebuilt using the automatically generated report, and then redeployed for another use.

Stored item and kit information can also be used to perform various forms of monitoring and/or reporting related to inventory management. For instance, stored kit information can be analyzed to identify patterns of item consumption. Moreover, the stored information can be inspected to determine the location of kits containing expired items. These and other forms of monitoring and/or reporting can be performed either automatically or in response to user input. For instance, they can be performed according to a predetermined schedule or in response to certain event triggers. Alternatively, a user may simply request monitoring or a report as needed. For example, a pharmacy manager may log in to view consumption logs, usage logs and current inventory to make more informed decisions on which inventory to keep and which kits may require special attention.

The kit management system typically further comprises a user interface and one or more software applications allowing a user to access information regarding the status of kits. As an example, a software application may be used to generate and print a kit charge sheet or charge sheet with the contents and expiration dates of the items and a kit. As other examples, a software application may be used to generate inventory reports showing where kits are dispatched within a hospital, an expiration report indicating dispatched items that are expired or near expiration, consumption and usage reports with traceability to departments, code types, or patients. The kit management system can also comprise or be integrated with a real-time tracking system to maintain current information regarding kit locations. The real-time tracking system typically comprises electronic components associated with the kits and configured to transmit information from the kits to the information processing system to identify the kits' respective locations. Such tracking systems can also be combined with kit management software in order to update the information used to generate inventory reports.

As indicated by the foregoing, a kit management system according to certain embodiments can provide many potential benefits compared with conventional technologies. For example, the kit management system can provide more efficient verification and recording of kit contents, and more accurate monitoring of kits, items, and expiration dates. In certain embodiments, the kit management system may also provide data analysis capabilities for purposes such as patient billing, inventory tracking, and so on.

In certain embodiments described below, a pharmacy kit is managed using multiple acceptance criteria for at least one pharmacy kit segment. The use of multiple acceptance criteria means that a designated segment may be deemed to be satisfactorily stocked with different types, quantities, or concentrations of pharmacy items under different circumstances. For example, if there is a shortage of a pharmacy item typically used to stock the designated segment, one or more different pharmacy items may be accepted as alternatives during the shortage.

The described embodiments may facilitate the use of multiple acceptance criteria by providing an information processing system that allows users to define different rules for determining automatically whether a segment is successfully stocked under different circumstances. Such a definition may include one or more types of items and be associated with one or more operators to suggest how multiple types of items interact with each other. For example, if a designated segment of a pharmacy kit requires three vials of propofol at 20 ml each (e.g., a "first acceptance criterion"), but there was a shortage for that package size, a user could define a rule allowing two 50 ml packages (e.g., a "second acceptance criterion") or two 30 ml packages (e.g., a "third acceptance criterion") as alternative ways of stocking the kit. As another example, an alternate concentration or drug may be used where an alternate size is not available. In that situation, rules may be set to determine which alternate drug or drug combinations would satisfy the requirements of the kit. For instance, if there is no calcium chloride, calcium gluconate may be substituted.

The described embodiments may also allow these rules to be ranked in order of preference to avoid ambiguity of items in a pharmacy kit matching multiple rules at the same time. A pharmacy manager may define preferred rules that cause a system to prompt a user to stock a pharmacy kit in a suggested way. Such rules may be stored in a way that allows a user to query an amount of time that a secondary or tertiary rule is in effect for a particular segment. This information can further be used to suggest optimizations for a pharmacy kit template.

The described embodiments may also be used to generate various types of reports related to the management of pharmacy kits using multiple acceptance criteria. For example, one type of report may identify the most commonly used medications for particular kit segments, enabling a manager greater visibility into medication ordering based on what actually makes it into circulation. Another type of report may provide a history of changes made to kit templates, informing a pharmacy of volatility of certain templates and medication stock. Such a report may be helpful for many management and operational activities such as ordering drug inventory, for instance. Yet another type of report may be an inventory list (or "charge sheet") with specific billing codes. Such a report may show one of several billing codes for a segment depending on which acceptance criterion or stocking rule was used to stock the segment.

In certain embodiments, a system may also suggest a pharmacy kit configuration based on available inventory. For example, if a pharmacy kit allows for two different sizes of the same medication in a segment, and one size is on shortage, the system could guide a user to increase the medication in the segment based on the size that is not on shortage.

These and other embodiments may provide pharmacy managers with greater flexibly to handle situations related to shortages of pharmacy items, which may in turn increase efficiency in a hospital pharmacy. They may also increase safety by making kit processing more robust in the face of periodic variances in pharmaceutical inventory.

FIG. 1 is a block diagram of a system for managing pharmacy kits according to an embodiment of the inventive concept.

Referring to FIG. 1, system 100 comprises an information processing system 115 and an RFID reading station 110. System 100 is configured to automatically read and process information from a pharmacy kit 105. This allows relatively efficient monitoring and updating of the kit's contents.

RFID reading station 110 comprises an RFID reader configured to read RFID tags located on kit 105. During a typical read operation, the RFID reader interrogates RFID tags associated with respective items in kit 105, and it also interrogates any RFID tag associated with kit 105. As a consequence of the interrogation, the RFID reader receives information identifying each tag, and it conveys the information to information processing system 115. Based on the tag information, information processing system 115 identifies kit 105 and the items present. This can be accomplished, for instance, by relating the tag information to item or kit information stored in a computer database.

Once the kit and items are identified, information processing system 115 may process corresponding information in various ways, for example, by displaying it to a user, generating reports indicating missing or expired items, performing patient billing procedures based on any consumed items, or merely storing it for subsequent analysis. In certain embodiments, the kit and item information is managed as a list. For example, it can be stored and accessed in the form of a list in a computer database or other storage medium.

One of the most common ways of processing information captured from a kit is comparing the captured information with a template of the kit to determine whether the kit is satisfactorily stocked. The template of a kit defines items that are required to be placed in the kit. The template typically defines a plurality of item segments (or "segments") to be included in the kit, where each item segment corresponds to a class or type of items and/or additional segments to be included in specific quantities. For instance, an item segment may define a specific class of medications, such as ibuprofen, acetaminophen, adenosine, or albuterol. Where a segment includes one or more additional segments, the template is considered to have multiple segment "levels". In general, a template can have an arbitrary number of segment levels. An example of a template having multiple segment levels would be one containing a segment "analgesic", with the item "morphine" and a sub-segment "ibuprofen" containing items "Advil" and "Generic".

A segment of a kit is deemed to be satisfactorily stocked if the kit includes all of the items specified by at least one acceptance criterion associated with that segment. The term "acceptance criterion" here denotes a set of one or more rules that determines items that can be accepted (or required) as fulfilling the requirements for a particular segment under specified circumstances. For instance, one rule may define a "first acceptance criterion" that accepts a first type of medication to stock the segment under normal circumstances, and another rule may define a "second acceptance criterion" that accepts a second type of medication to be stocked in the segment where there is a shortage of the first type of medication. In other words, different rules may govern how a segment can be satisfactorily stocked under normal or shortage conditions. In general, the items that may be used to satisfactorily stock a segment may be, e.g., medications of different types (e.g., brands, formulations, etc.), concentrations, quantities, etc. These items are generally identifiable by distinct NDC or UPC identifiers. Circumstances that trigger the use of a different acceptance criteria are referred to as kit stocking contingencies. A shortage of items is one common example of a kit stocking contingency, but other contingencies are possible.

System 100 may occasionally aggregate last known status information for each kit that has been read, and it may then determine whether any action is required to resolve expiration issues, missing item issues, or extra item issues in all of the kits in a hospital or other facility. These actions can be performed, for example, on a periodic basis, in response to particular events, or in response to a user request.

System 100 may occasionally aggregate last known status information for each kit that has been read, and it may then determine whether any action is required to resolve expiration issues, missing item issues, or extra item issues in all of the kits in a hospital or other facility. These actions can be performed, for example, on a periodic basis, in response to particular events, or in response to a user request.

In addition to storing current or most recent information regarding kits, system 100 may also store a virtual history for each kit. Such a virtual history may include, for example, a record of each transaction involving the kit since the time it was tagged. Such transactions may include, for example, scans, database queries, updates such as restocking or removal of items, the occurrence of kit stocking contingencies and the use of alternative acceptance criteria when stocking segments, and so on. The virtual history may be maintained by information processing system 115, for example, and it may be output in the form of a report in response to a user request. In addition, the virtual history may be used to gather data or statistics that may be useful for planning future tasks such as kit updates, item restocking, and so on.

Kit 105 can be associated to a location or responsible person, such as a physician. This association can then be stored in system 100, and it can be used to quickly determine the location of kit 105 after deployment. The location of kit 105 can also be determined and/or updated by associating its RFID tag with a real time location system. In addition, kit 105 may be associated with a patient identifier or billing identifier and any missing items may be marked as being consumed by that billing or patient identifier. Such billing information may be stored either in system 100, in a separate system or in both system 100 and a separate system. System 100 may retrieve or update some or all of the billing information when a kit is read and items may or may not be consumed.

Where kit 105 contains prescription pharmaceuticals, the facility may be required to comply with requirements set by a state board of pharmacy. The precise regulations may vary from state to state, but can include requirements such as a mandatory visual inspection of kit 105 prior to deployment, or an item-by-item determination of each item type, lot number and expiration date. Other board of pharmacy requirements may include documentation to be included in kit 105 to verify completeness and accuracy of expiration data or a label on the outside of kit 105 to indicate the last check of the kit and the next expiring item in the kit.

In some embodiments, system 100 is configured to store relevant board of pharmacy requirements and verify that each step has been completed. System 100 can also be configured to compute steps automatically where allowed by regulations. Such steps may include, for example, printing documentation or labels, reading tags and verifying items, or requesting confirmation that a manual step has been completed. As these steps are completed, system 100 may record the name of the person who performed the steps. It may also confirm whether the person is authorized to perform the steps. In general, information regarding these and other steps can be recorded in system 100 using a log, database, or other storage format.

Although FIG. 1 shows RFID reading station 110 and information processing system 115 as separate features, they are not required to be physically or functionally separate.

For instance, information processing features could be integrated with parts of RFID reading station 110, such as an RFID reader. In general, the physical and functional implementation of system 100 can be partitioned arbitrarily between various forms of hardware, software, firmware, etc., as will be recognized by those skilled in the art.

In addition, the physical and functional implementation of system 100 can be distributed arbitrarily across multiple devices, systems, or network components. For example, in some embodiments, information processing system 115 may include or be integrated with wireless mobile devices in order to convey information remotely. One potential use of such a configuration would be to transmit kit notifications to remote users via push email or SMS text messaging, or subscription based data feeds. Such notifications could be used, for instance, to alert users that an updated kit is available, that a kit should be returned to the pharmacy, that a checked-out kit requires updates due to item expiration, and so on. Another potential reason to integrate information processing system 115 with remote components is to receive updates of kit templates and item master data. For example, some or all of a kit template or item master data may be received from an external system. The received item master data could indicate, for example, that an item has been recalled or changed in some material respect.

Figure 2:
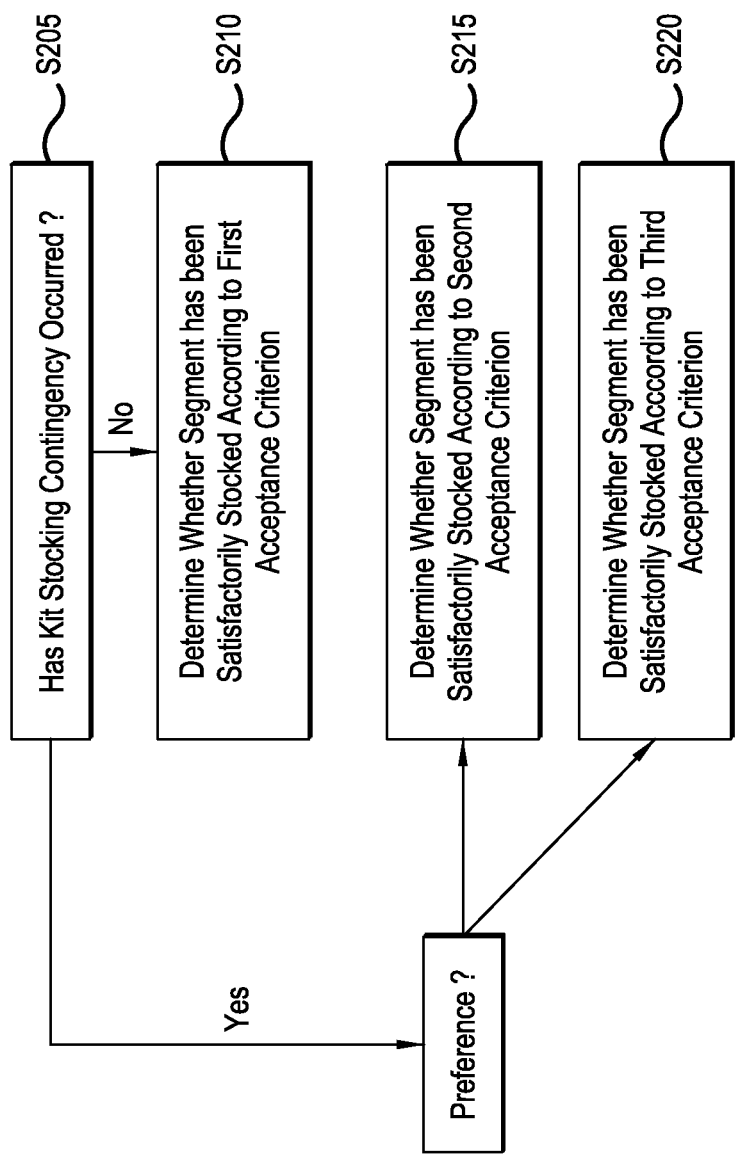
FIG. 2 is a flowchart illustrating a method of managing pharmacy kits according to an embodiment of the inventive concept.

FIG. 2 is a flowchart illustrating a method of managing pharmacy kits according to an embodiment of the inventive concept. The method of FIG. 2 is typically used to verify that a kit has been successfully stocked.

Referring to FIG. 2, the method comprises determining whether a kit stocking contingency has occurred with respect to a segment of the pharmacy kit (S205). The kit stocking contingency may be, for instance, a shortage of at least one pharmacy item corresponding to the first acceptance criterion. In general, a shortage may occur where there is inadequate supply of the at least one pharmacy item to meet current needs or expected needs of a medical facility served by a pharmacy. Determining that a kit stocking contingency has occurred may comprise, for instance, receiving a shortage notification for the at least one pharmacy item corresponding to the first acceptance criterion. Alternatively, it may comprise examining an inventory level and detecting a shortage where the inventory level falls below a defined threshold.

The method further comprises, as a consequence of determining that the kit stocking contingency has not occurred (S205=No), determining whether the segment has been satisfactorily stocked according to a first acceptance criterion (S210). This can be accomplished, for instance, by evaluating kit related information captured by a system such as that illustrated in FIG. 1. The evaluation may include, e.g., comparing the information with a list of required pharmacy items specified by a template under the first acceptance criterion, or comparing the information against one or more rules defined according to the first acceptance criterion.

The method still further comprises, as a consequence of determining that the kit stocking contingency has occurred (S205=Yes), determining whether the segment has been satisfactorily stocked according to a second or third acceptance criterion different from the first acceptance criterion (S215 or S220). In other words, where a kit stocking contingency arises, the method may use a different criterion to determine whether the segment is satisfactorily stocked. As illustrated by a box labeled "Preference?", the second or third criterion may be selected according to a user preference (or hierarchical ranking), which may be defined within a particular implementation of the method.

The first through third acceptance criteria may specify, for instance, different types, sizes, or concentrations of items (e.g., medications) that can be used to stock the segment. The different types of items may also be associated with different operators (e.g., different authorized professionals), such that where a kit is being stocked by one type of operator, the first through third acceptance criteria may be satisfied by a first type of pharmacy item, and where the kit is being stocked by another type of operator, the first through third acceptance criteria may be satisfied by a second type of pharmacy item different from the first type of pharmacy item.

The method may further comprise determining whether an additional kit stocking contingency has occurred, and as a consequence of determining that the additional kit stocking contingency has occurred, determining whether the segment of the pharmacy kit has been satisfactorily stocked according to one or more additional acceptance criterion different from the first and acceptance criteria. In other words, the method may be extended to use not only secondary acceptance criteria, but also tertiary acceptance criteria, and so on. In general, where multiple acceptance criteria are used under different circumstances, those additional acceptance criterion can be ranked in order of user preference. Moreover, those rankings may differ according to the user who is performing a stocking or kit checking procedure.

The method may still further comprise operations allowing a user to define the rules for determining whether a segment is satisfactory stocked. For instance, the method may comprise receiving a user input to define one or more such rules for the first criterion or the second criterion.

Figure 3:
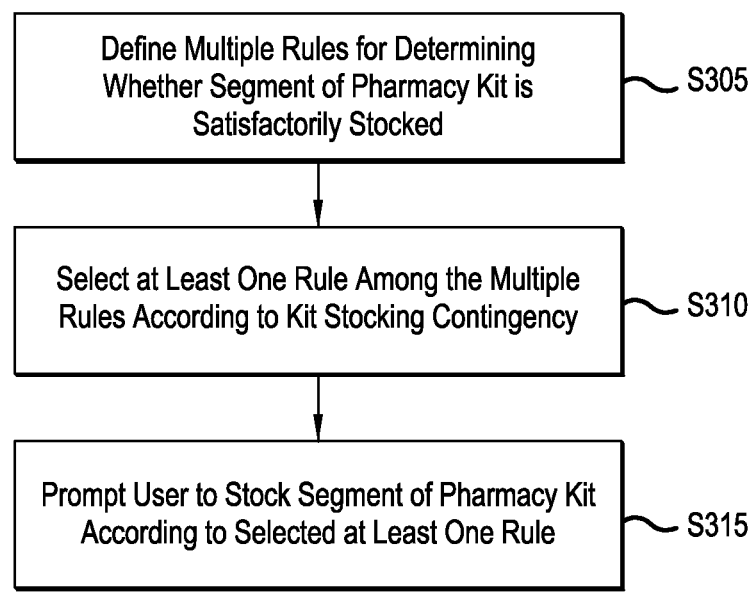
FIG. 3 is a flowchart illustrating a method of managing pharmacy kits according to another embodiment of the inventive concept.

FIG. 3 is a flowchart illustrating a method of managing pharmacy kits according to another embodiment of the inventive concept. The method of FIG. 3 is typically used to ensure proper stocking of a pharmacy kit.

Referring to FIG. 3, the method comprises defining, in an electronic information processing system (e.g., system 100), multiple rules for determining whether a segment of a pharmacy kit is satisfactorily stocked (S305). As an example, one rule may require that the segment be stocked with a first type, size, quantity, or concentration of a medical item when there is no shortage of that item, and another rule may require that the segment be stocked with something other than the first type, size, quantity, or concentration where there is a shortage.

The method further comprises selecting, by the electronic information processing system, at least one rule among the multiple rules according to a kit stocking contingency (S310). This selection is typically performed automatically when there is a shortage or other kit stocking contingency. It may be initiated, for instance, in response to reception of an automated shortage notification, in response to user input indicating a shortage, or in response to an inventory level falling below a defined threshold. Additionally, the multiple rules may be ranked in order of user preference and selected according to the ranking.

The method still further comprises prompting, by the electronic information processing system, a user to stock the segment of the pharmacy kit according to the selected at least one rule. (S315). For instance, the system may display an interface instructing the user to stock the segment with a particular type, size, concentration, or quantity of a pharmacy item. The system may then allow the user to rescan the kit to confirm proper stocking of the segment.

The methods of FIGS. 2 and 3 may each further comprise generating various types of reports or otherwise providing information to a user based on the use of alternative acceptance criteria or rules. The reports or other information may be generated or provided either automatically or in response to a user query. For instance, system 100 may receive a query from a user requesting an amount of time for which a selected rule is to be in effect and then display the requested amount of time to the user. This information may be a useful indicator of the duration of an item shortage, for instance. As other examples, the method may generate a report indicating relative quantities of pharmacy items used to stock the segment according to the multiple rules, a report indicating a history of changes made to a template of the pharmacy kit, or a charge sheet comprising billing information for pharmaceutical items corresponding to the selected at least one rule.

FIGS. 4 through 10 show various examples of interfaces that may be used to present and/or receive information from a user during the methods described above with reference to FIGS. 2 and 3. Such interfaces may be used in conjunction with a system such as that illustrated in FIG. 1, for example.

FIG. 4 shows an interface 400 for adding a fill option to a segment of a pharmacy kit according to an embodiment of the inventive concept. A fill option specifies one or more pharmacy items that can be used to satisfactorily stock the segment under designated circumstances. In other words, it corresponds to a rule for stocking the segment with the pharmacy items.

Referring to FIG. 4, interface 400 comprises fields allowing a user to enter information identifying a formulary item, including an NDC, manufacturer, item name, strength, and package size. It further comprises a field allowing the user to enter a segment that may be filled by the formulary item, and a field allowing the user to designate a rule for using the formulary item within the segment, namely a rule designating the formulary item as a "preferred fill option" or as an "alternate fill option". The preferred fill option status may be used, for instance, where the designated formulary item is to be included in a kit under default circumstances, and the alternate fill option status may be used, for instance, where the designated formulary item is to be included in a kit because of a shortage.

FIG. 5 shows an interface 500 for modifying fill options for a segment of a pharmacy kit according to an embodiment of the inventive concept.

Referring to FIG. 5, interface 500 comprises fields allowing a user to add or remove fill options to a segment, to specify the quantity associated with a fill option, or to set a billing code for a fill option. In the illustrated example, a user has searched for possible new fill options by entering the search term "epi" into a search field. As a result, the interface has displayed various search results that include the entered term. A user can include any of those search results as a fill option by clicking on "+Add". In the illustrated example, three fill options have already been added to the segment. Any of those fill options can be removed by clicking on "x Remove". Moreover, one of those options has been selected, as indicated by shading. The quantity and billing code at the top of interface 500 correspond to the selected fill option.

FIG. 6 shows an interface 600 for adding, removing, or modifying fill options for a segment of a pharmacy kit according to an embodiment of the inventive concept.

Referring to FIG. 6, interface 600 shows a segment that belongs to a general operating room (OR) kit. The segment is specified by entering or selecting a segment name in a field near the top of interface 600. In the illustrated example, the segment has two preferred fill options and three alternate fill options. The preferred and alternate fill options can be added, removed, or modified by clicking on appropriate portions of interface 600. The entire segment can be deleted by clicking "Delete Segment" at the bottom of interface.

FIG. 7 shows an interface 700 indicating that an alternate fill option has been used to stock a segment of a pharmacy kit, according to an embodiment of the inventive concept.

Referring to FIG. 7, interface 700 shows a partial summary of items included in various segments of a kit that has been scanned. In the summary of a segment "Ampicillin 1 g", an icon indicates that a non-preferred fill option was used to stock the kit. This may indicate, for example, that the preferred fill option was on shortage.

FIG. 8 shows an interface 800 with icons indicating that alternate fill options exist for certain segments of a pharmacy kit, according to an embodiment of the inventive concept.

Referring to FIG. 8, interface 800 comprises a field that allows a user to select a kit master, which specifies the segments and corresponding items for a kit. In the illustrated example, the selected kit master is for an "Anesthesia C-section Tray" kit. Interface 800 further comprises a field displaying each of the segments of the selected kit master, with icons next to segments having multiple fill options. For instance, an icon to the left of the name label on a segment "Diphenhydramine 50 mg/ml vial" indicates that there is more than one fill option for this segment. For each of the segments, interface 800 displays the name of a primary fill option, and it also provides an option to hide or show alternative fill options for the segments with multiple fill options.

FIG. 9 shows an interface 900 identifying the contents of a segment of a pharmacy kit, together with an indication that alternate fill options were used to stock the segment, according to an embodiment of the inventive concept.

Referring to FIG. 9, interface 900 may be displayed to a user after the kit is scanned. It contains an icon below the segment name "Amiodarone inj 150 mg/3 ml" to indicate that at least one of the scanned items matches a non-preferred fill option for this segment.

FIG. 10 shows an interface 1000 displaying exceptions in a kit with an icon to indicate that missing items can be restocked to match one of multiple rules for a segment, according to an embodiment of the inventive concept.

Referring to FIG. 10, interface 1000 may be displayed after a kit is scanned. It displays exceptions in the scanned kit, which are features or occurrences that are deemed to require user notification. In the illustrated example, the exceptions include items that will expire soon, missing items, extra items, and wrong items. Next to the missing items, interface 1000 includes an icon indicating that multiple fill options are available. It also includes an indication of an expected quantity of those items (e.g., an amount that may be needed to fill expected demand), an actual quantity of those items in inventory, and a shortage, which is defined as a difference between the expected and actual quantities. This information may assist a user in taking appropriate action, such as either stocking the missing items using a primary fill option in the event that there is adequate supply, or stocking the missing items using an alternate fill option in the event that there is a shortage.

Figure 11A:
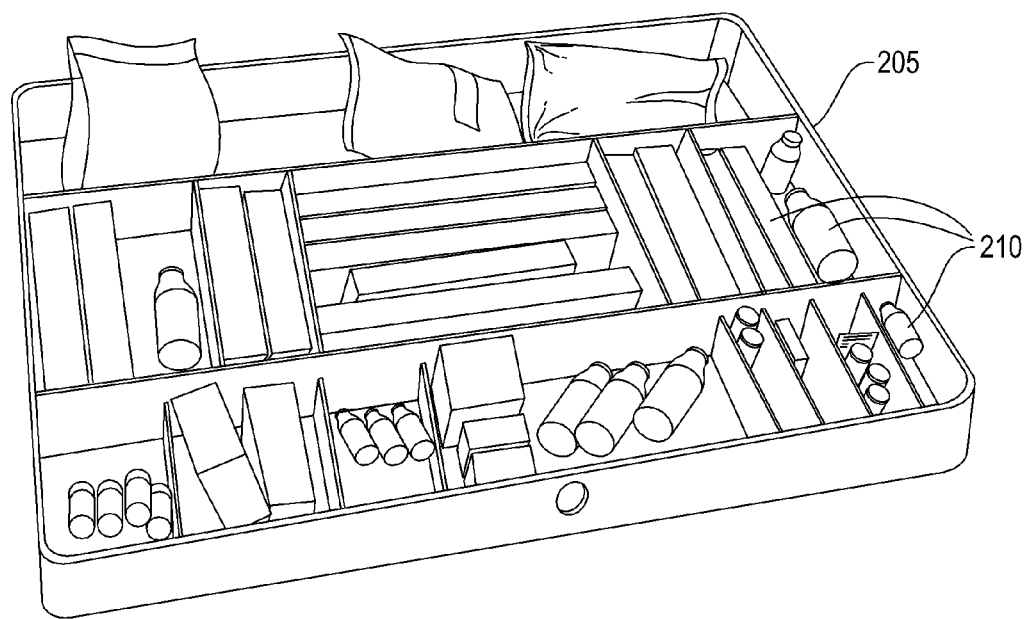

FIGS. 11A through 11C are diagrams illustrating a pharmacy kit according to an embodiment of the inventive concept. In particular, FIG. 11A shows an example of a kit tray comprising multiple items having RFID tags, FIG. 11B shows an example of a partial template associated with the kit, and FIG. 11C shows an example of a partial kit record for the kit. The kit of FIGS. 11A through 11C represents one example of pharmacy kit 105 shown in FIG. 1.

Referring to FIG. 11A, kit 105 comprises a container 205 and items 210. Container 205 is shown as a tray in FIG. 11A, but this is merely one example of a container that can be used to carry items 210. Alternative examples include boxes, canisters, bags, coolers, and various others. Although not shown in FIG. 11A, kit 105 could further comprise a cover, such as a lid, that can be used to enclose items 210 prior to deployment. Additionally, the cover can be sealed onto container 205 to prevent tampering between deployment and use of kit 105. In general, where kit 105 is susceptible to opening or closing (e.g., where it has a lid or other covering), it can be read in an open configuration or a closed configuration.

Items 210 typically include medicines or other medical supplies that may be stocked by a pharmacy. As shown in FIG. 11A, items 210 can have various different forms of packaging. For example, they can be packaged in vials, bags, boxes, bottles, and other forms. These different forms of packaging may also comprise different materials, such as glass, plastic, paper, cardboard, foam, or metal.

Due to the different types of packaging and materials, items 210 may be tagged with RFID tags having different shapes or types. As one example, RFID tags placed on metal bags may be subject to electromagnetic interference (EMI) from the metal. Accordingly, to prevent EMI, RFID tags connected to metal bags may have a foam backing or other form of insulation to create separation from the bags. Such tags may be referred to as metal-mount tags. As another example, RFID tags attached to small vials or bottles may potentially occlude label information on the vials. Accordingly, to prevent occlusion, RFID tags having a transparent adhesive portion may be attached to vials, bottles, or other types of packages. Such tags may be referred to as transparent tags.

Kit 105 is typically built by manually placing items 210 in container 205. This is typically accomplished by a pharmacist or other competent medical professional after items 210 have been labeled with RFID tags and stocked in the pharmacy. For example, a pharmacist may visit pharmacy shelves to collect items 210 and place them in container 205.

Referring to FIG. 11B, an example template defines items to be placed in kit 105. More specifically, the template defines a plurality of item segments (or "segments") to be included in kit 105, where each item segment corresponds to a class or type of items and/or additional segments to be included in specific quantities. For instance, an item segment may define a specific class of medications, such as ibuprofen, acetaminophen, adenosine, or albuterol. Where a segment includes one or more additional segments, the template is considered to have multiple segment "levels". In general, a template can have an arbitrary number of segment levels. An example of a template having multiple segment levels would be one containing a segment "analgesic", with the item "morphine" and a sub-segment "ibuprofen" containing items "Advil" and "Generic".

For simplicity, FIG. 11B shows example segments in generic form, i.e., "medicine bottle 1", "medicine vial 2", etc. The segment "medicine bottle 1", for example, indicates that kit 105 is to include one or more bottles of a first type of medicine (e.g., a bottle of ibuprofen). Similarly, the segment "medicine vial 2" indicates that kit 105 is to include one or more vials of a second type of medicine (e.g., a vial of adenosine), and so on. Although each segment in FIG. 11B is associated with a particular type of packaging, such as a bottle, vial, or bag, segments are not necessarily limited by package type. For instance, a segment could be defined more broadly based on medicine type alone.

The template further defines a set of permissible items that can be used to satisfy each segment. The permissible items may correspond to different brands or other forms of each item corresponding to the segment. These items are generally identifiable by distinct NDC or UPC identifiers. As an example, a segment defined as a "bottle of ibuprofen" may be satisfied by a either a bottle of Advil or a bottle of generic ibuprofen. For simplicity, FIG. 11B shows the items associated with each segment in generic form, i.e., "product A", "product B", etc. Accordingly, the segment "medicine bottle 1" may be satisfied by two different products "A" and "B", the segment "medicine vial 2" may be satisfied by three different products "C", "D", and "E", and so on.

The template still further defines a quantity of items to be included in kit 105 for each segment. For example, based on the template of FIG. 11B, kit 105 is to include one item corresponding to "medicine bottle 1" (e.g., one bottle of ibuprofen), three items corresponding to "medicine vial 2", two items corresponding to "medicine bag 3", and so on. As a more concrete example, a segment "Pain Medication" could have permissible items "Tylenol" or "Advil", with a quantity of two, which could be satisfied by two bottles of Tylenol, two bottles of Advil, or one of each, for instance.

In general, the quantity can be zero or more. Where the quantity is greater than one, each item of a particular segment can be satisfied by any combination of the permissible items for that segment. For example, if there are three permissible items and the required quantity is three, the requirement may be satisfied by three of the same permissible item, one of each, etc. For instance, some kits may allow the stock of adenosine vials to be satisfied by different product brands. Alternatively, the template may require that multiple instances of the same item be selected, or that only certain combinations of items are permitted. Moreover, the template may include restrictions on the items that can be included in combination from among different segments.

Although the template determines the contents to be included in the kit under most circumstances, there are occasions where deviation from the template will be permitted. One of these occasions is a national shortage of one or more items to be included in the kit. When there is a national shortage of a particular item, certain substitutions or omissions of the item may be allowed. For example, if sodium bicarbonate is on national shortage, a kit may be permitted to include a suitable substitute for sodium bicarbonate, or it may be permitted to be deployed without sodium bicarbonate or any substitute.

The procedure for managing items under shortage may be defined in a variety of ways. For example, allowable substitutes for national shortage conditions may be embedded in the template itself and then triggered by information processing system 115 when a shortage arises. As an alternative example, information processing system 115 may simply ignore certain restrictions in a template when a shortage arises.

Referring to FIG. 11C, a kit record comprises information regarding the contents of a kit that has been built in a pharmacy and verified through the use of RFID reading station 110. In the example of FIG. 11C, the information comprises the name of each segment in the kit, and specific details of each item in each segment. The specific item details include a brand name, an item name, an NDC identifier, a lot number, medicine strength or concentration, and an expiration date. The item details may further include information indicating whether an item has a fixed expiration date or one that varies based on time away from a refrigerator. Where the item has a variable expiration date, the item details may indicate whether the item has been removed from the refrigerator, and if so, at what time or date.

The kit record is typically generated by RFID reading station 110 or information processing system 115 upon verifying or re-verifying the kit. It can then be compared to a corresponding template to determine whether the kit has missing or expired items, or it can be stored in information processing system 115 for subsequent comparisons, updates, or analyses.

Figure 12A:
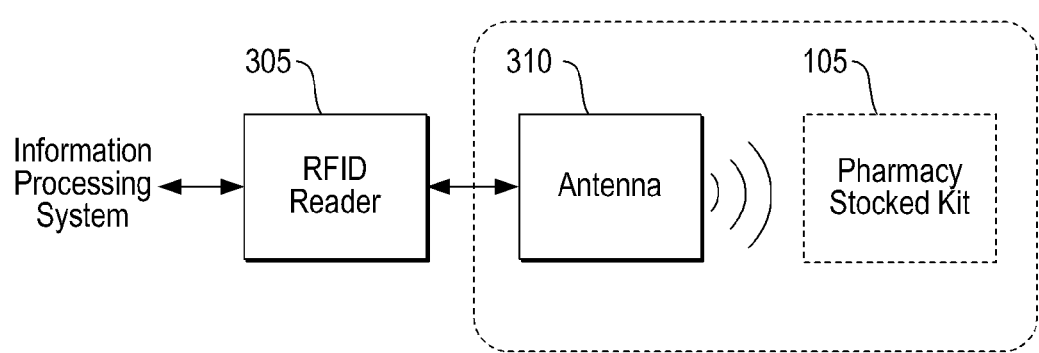

FIGS. 12A and 12B are diagrams of RFID reading station 110 of FIG. 1 according to an embodiment of the inventive concept. In particular, FIG. 12A is a block diagram illustrating electronic equipment associated with RFID reading station 110 according to an example embodiment, and FIG. 12B is a schematic diagram of a container configured to receive kit 105 during a read operation of RFID reading station 110.

Referring to FIG. 12A, RFID reading station 110 comprises an RFID reader 305 and an antenna 310. Antenna 310 is located within a container 315 designed to receive kit 105 during a read operation. RFID reader 305 controls antenna 310 to communicate with RFID tags associated with items of kit 105, as well as any RFID tag associated with the kit itself. In addition, RFID reader 305 receives and processes communications received by antenna 310 from kit 105. Although RFID reader 305 is shown outside of container 315, it could alternatively be included within container 315. Moreover, although RFID reader 305 and antenna 310 are shown as two separate components, they could alternatively be integrated into a single component or divided into additional components.

In a typical read operation, RFID reader 305 controls antenna 310 to interrogate any RFID tags within container 315. In response to the interrogation, the RFID tags communicate information to RFID reader 305 via antenna 310. The communicated information is typically associated with corresponding information stored in a database, such as NDC identifiers, lot numbers, and expiration dates for individual items, and a kit identifier for the kit as a whole. RFID reader 305 communicates the received information to information processing system 115 for storage and/or comparison with a template.

Referring to FIG. 12B, container 315 comprises an enclosed space for receiving kit 105. The left side of FIG. 12B shows container 315 with doors opened to receive kit 105, and the right side of FIG. 12B shows container 315 with doors closed to perform a read operation. The use of an enclosed space to allows RFID tags to be read without interference from objects in the surrounding environment, such as false positives from RFID tags on items not belonging to kit 105. Accordingly, container 315 may be formed of a material designed to provide electromagnetic shielding, such as a metal box.

In some embodiments, RFID reading station 110 is restricted to receiving only one kit at a time. This restriction may be imposed in a variety of ways, for instance, by configuring an enclosure to accommodate only one kit container or interrogating kit tags prior to scanning to ensure that no more than one kit tag is present. In certain alternative embodiments, RFID reading station 110 may be specifically configured to allow concurrent scanning of multiple kits. For example, two kits could be placed in RFID reading station 110, scanned concurrently, and then assigned to a common location or person, such as a particular cart, room, physician, etc. Moreover, such a common assignment may be recorded in information processing system 115 to allow joint analysis or tracking of more than one kit.

Figure 13:
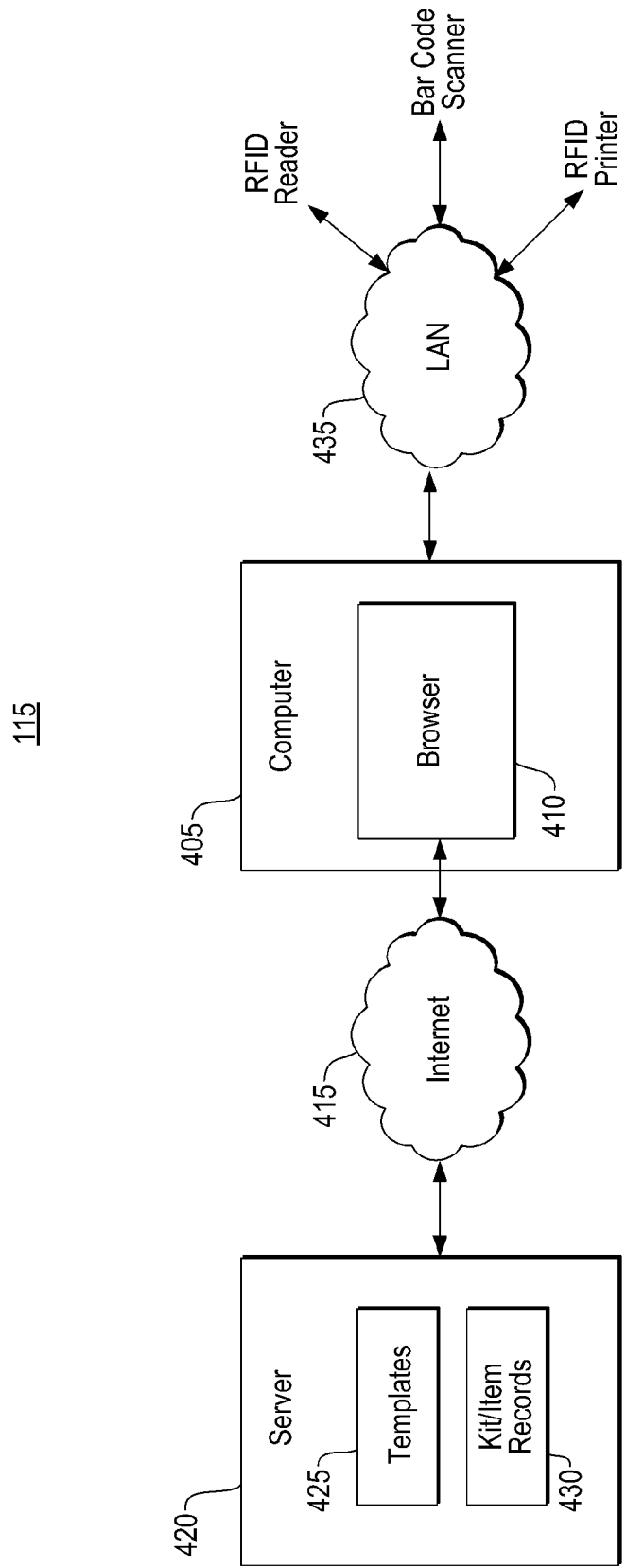
FIG. 13 is a diagram of an information processing system in the system of FIG. 1 according to an embodiment of the inventive concept.

FIG. 13 is a diagram of information processing system 115 according to an embodiment of the inventive concept. In the embodiment of FIG. 13, various features of information processing system 115 are connected in a networked configuration. However, in alternative embodiments these components could be in alternative configurations, e.g., with components directly connected, physically integrated, or functionally partitioned in other ways.

Referring to FIG. 13, information processing system 115 comprises a computer 405 and a server 420. Computer 405 and server 420 are connected to each other via the internet 415, and computer 405 is connected to an RFID reader, a bar code reader, and an RFID printer through a local area network (LAN) 435.

Computer 405 comprises a browser 410 that receives kit information from the RFID reader via LAN 435 and communicates with server 420 through the internet 415. Server 420 stores templates 425, which typically include kit master templates and item master templates. Server 420 also stores records 430, which include information regarding individual kits and items.

Although server 420 is shown as a single unit in FIG. 13, it may comprise more than one device, such as multiple local and/or central computers. In addition, although server 420 is shown to be connected with a single computer, it may be connected to additional or alternative devices, such as other local computers, mobile devices, and so on. Moreover, although server 420 is shown to receive information from a single RFID reader, it could also receive information from other RFID readers. For example, information processing system could be connected to multiple RFID reading stations through the internet 415.

The RFID printer can be used to print RFID tags automatically when a kit is being built or updated. For example, an RFID tag can be printed for a new item by scanning the item's bar code using a bar code scanner connected to computer 405, accessing server 420 to associate a particular RFID tag with the item, and then printing the RFID tag.

Figure 14:
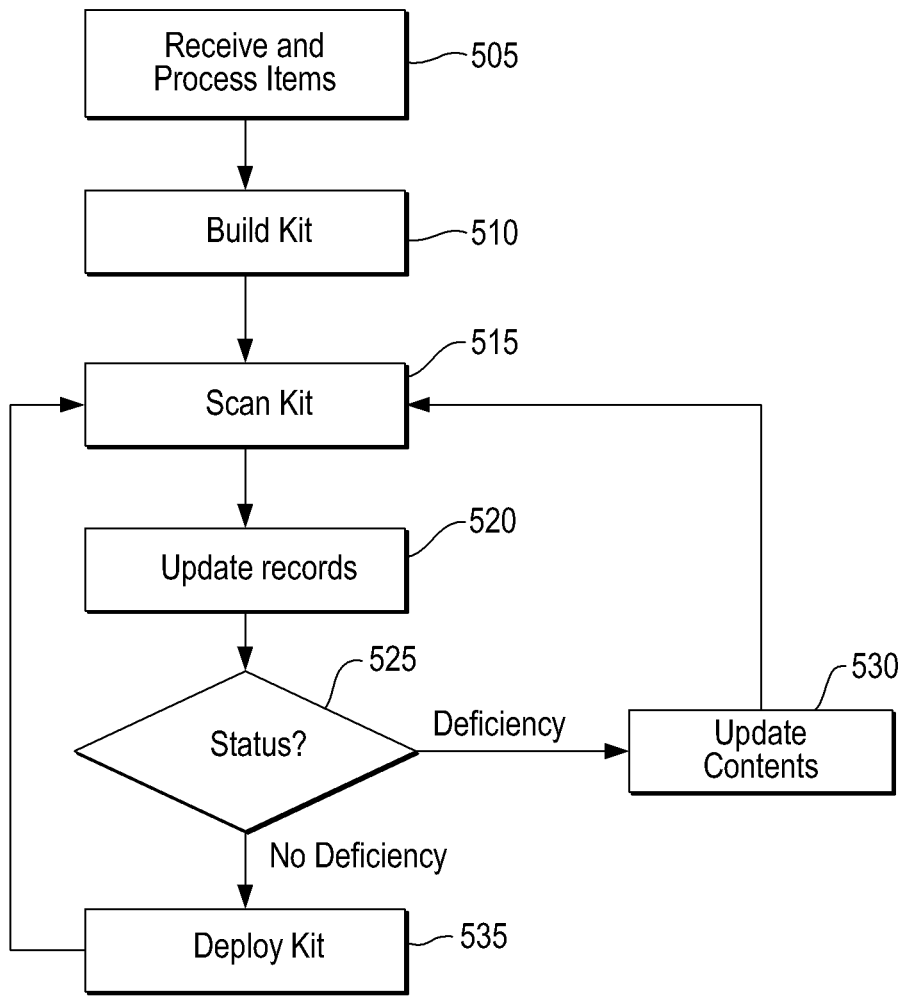
FIG. 14 is a flowchart illustrating a method of managing pharmacy kits according to an embodiment of the inventive concept.

FIG. 14 is a flowchart illustrating a method of managing pharmacy kits according to an embodiment of the inventive concept. The method of FIG. 14 is typically performed by a pharmacist or other medical professional associated with a hospital pharmacy. For explanation purposes, it will be assumed that the method of FIG. 14 is performed using system 100 of FIG. 1. However, the method is not limited to a particular system. In the description that follows, example method steps will be indicated by parentheses (XXX) to distinguish them from device or system components.

Referring to FIG. 14, the method begins with a pharmacy receiving and processing kit items (505). The items typically arrive in bulk at the pharmacy and are processed by tagging them with RFID tags and recording them in an inventory system. Next, a kit is built from tagged items in the pharmacy inventory (510), and the kit is scanned using RFID reading station 110 (515). The scan detects RFID tags of kit items and the kit itself and transmits corresponding information to information processing system 115.

Information processing system 115 updates stored records to reflect the scanning (520). In the update, a database in information processing system 115 is updated to reflect the scanned kit contents. For example, the database may be updated to reflect the presence of any new or replaced items, along with their expiration dates. The database may also be updated with other information, such as the name of the person who last modified the kit contents, a location to which the kit is to be deployed, a patient to be billed for consumption of kit items, and so on.

Based on the updated records, information processing system 115 performs a status check to verify the contents of the kit (525). The status check typically involves forming a list of items based on the transmitted information or updated records and comparing the list against a kit template. It may also involve comparing the updated kit information against information obtained in prior scans, or evaluating the kit information in light of certain business rules, such as billing protocols.

If the status check indicates a deficiency in the kit (525="Deficiency"), such as missing or expired items, the kit contents are updated (530), and the method returns to step 515 where the kit is re-scanned. The update can be performed, for example, by replacing any expired items or inserting missing items. Otherwise, if the status check indicates no deficiency in the kit (525="No Deficiency"), the kit is deployed for use in the hospital or other facility served by the pharmacy (535).

The updating of records and status check are typically performed any time the kit is scanned, as indicated by the flow of FIG. 14. This can take place under a variety of circumstances, such as when a kit is first built and verified, when the kit is checked-in to the pharmacy for storage, or when the kit is checked-out of the pharmacy for use.

Deployment of the kit may involve, for example, transporting it to a specific location of the hospital, checking it out to a particular individual, or merely storing it within the pharmacy. Following deployment, steps 515 through 535 may be repeated any number of times as needed. For example, the kit may be re-scanned and updated following each use or it may be periodically updated at specified times, such as daily, weekly, or whenever an expired item is noted in information processing system 115.

Figure 15:
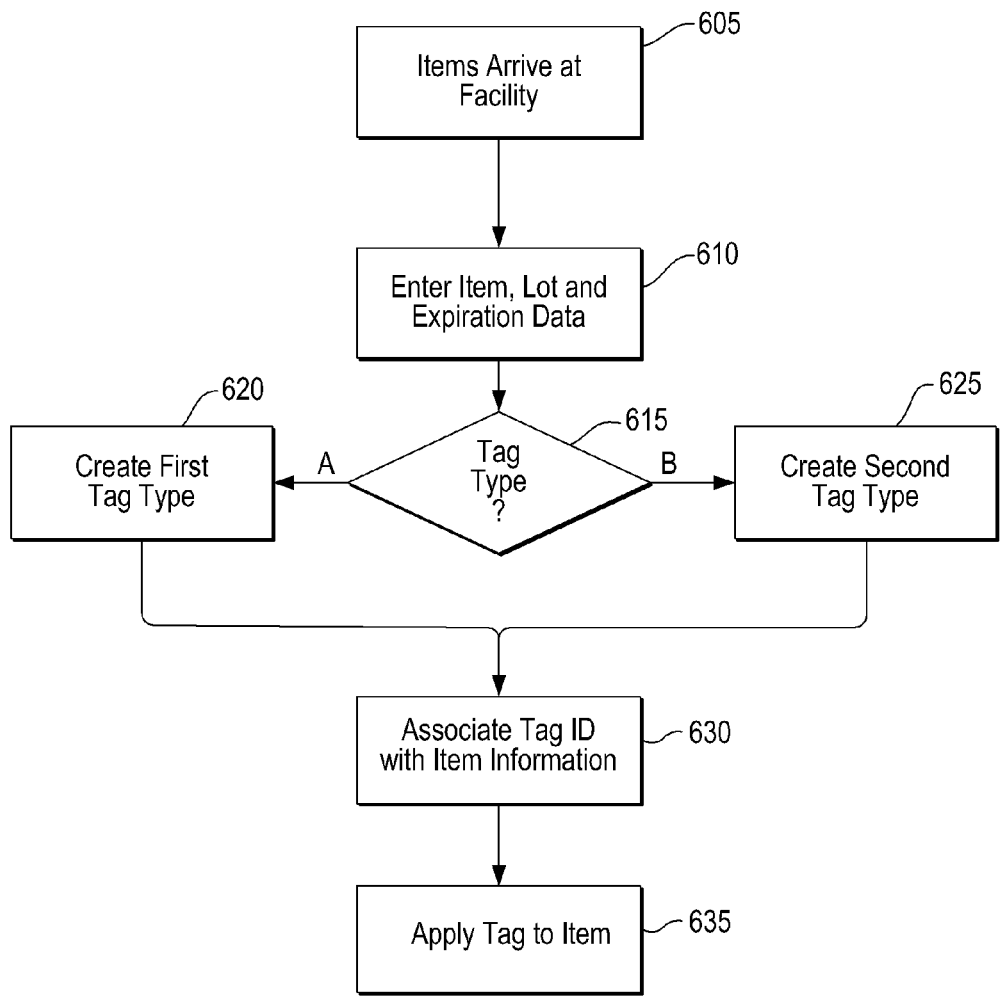
FIG. 15 is a flowchart illustrating a method of receiving and processing items for a pharmacy kit according to an embodiment of the inventive concept.

FIG. 15 is a flowchart illustrating a method of receiving and processing items for a pharmacy kit according to an embodiment of the inventive concept. The method of FIG. 15 is an example of step 505 of FIG. 14.

Referring to FIG. 15, items arrive at a facility (e.g., a hospital) from a third party manufacturer, distributor, or supplier (605). In some circumstances, the items may have RFID tags when they arrive at the facility. Accordingly, system 100 may scan the items and look up item information from the third party or an additional third party. Such information may include, for example, item master data, item lot data, and item expiration dates. If the items are not already tagged, item information may be entered into system 100 using a bar code scanner as described above, or by manual user input (610).

Based on the item information, system 100 determines whether each item requires a first type of tag (illustrated as type "A") or a second type of tag (illustrated as item type "B") (615). This determination is typically performed based on the type of the item or its packaging. For example, items having metal packaging such as metal bag, etc., may require an RFID tag having a thicker insulation layer (e.g., foam) to prevent it from experiencing EMI from the metal. Other types of items, such as glass or plastic packages, may not require such an RFID tag. Although the method of FIG. 15 shows an example using two different tag types, the described method is not limited to two tag types, and could be performed with additional tag types. Following the determination of the tag type, system 100 creates the first type of tag (620) or the second type of tag (625).

In creating the tags, system 100 may optionally perform automatic detection of whether it is attached to an RFID printer. If such an attachment is detected, it may control the RFID printer to print an RFID tag having a unique identifier for each item in the kit. Otherwise, a user may manually enter a unique tag identifier for each item into system 100. The manually entered identifiers can be determined, for example, based on the labeling of already printed RFID tags.

Next, system 100 associates the unique identifiers with the stored item information (630), allowing the item information to be retrieved subsequently when the RFID tags are scanned. Finally, the RFID tags are attached to corresponding items (635).

Figure 16:
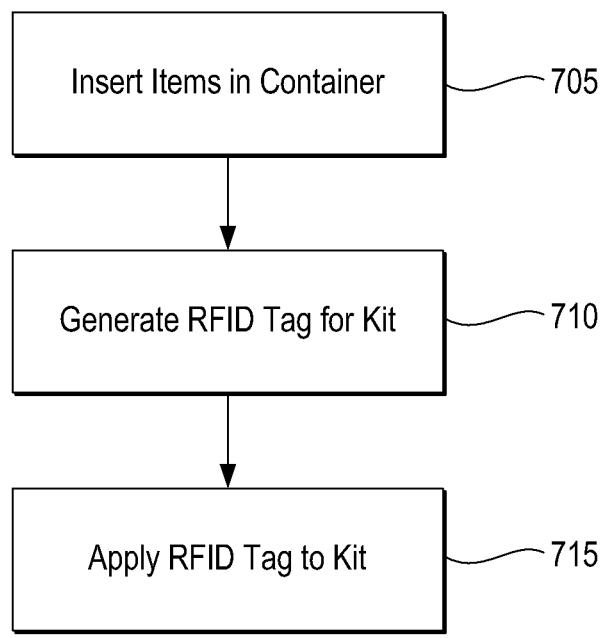
FIG. 16 is a flowchart illustrating a method of building a pharmacy kit according to an embodiment of the inventive concept.

FIG. 16 is a flowchart illustrating a method of building a pharmacy kit according to an embodiment of the inventive concept. The method of FIG. 16 is an example of step 510 of FIG. 14.

Referring to FIG. 16, the method comprises inserting tagged items into a container (705), generating an RFID tag for the kit (710), and applying the RFID tag to the kit (715). The method may further comprise sealing the kit; however, the sealing is typically performed after the kit has been scanned. Where system 100 is connected to an RFID printer, the kit's RFID tag can be generated using the printer, similar to the method of FIG. 15. Otherwise, a preprinted RFID tag can be used, and the tag's number can be manually entered into system 100 as in the method of FIG. 15. The sealing can be performed, for example, using a shrink wrap material, an adhesive, a sticker, or various other known techniques. In general, the term seal or sealing, as used herein, should not be construed in an overly formal sense—for example, it does not require an airtight seal—but rather it merely refers to a mechanism for ensuring that the contents of the kit are not tampered with as long as a seal remains in place or unbroken. Moreover, some seals used in conjunction with RFID technology may allow RFID based detection of whether a seal is broken.

Figure 17A:
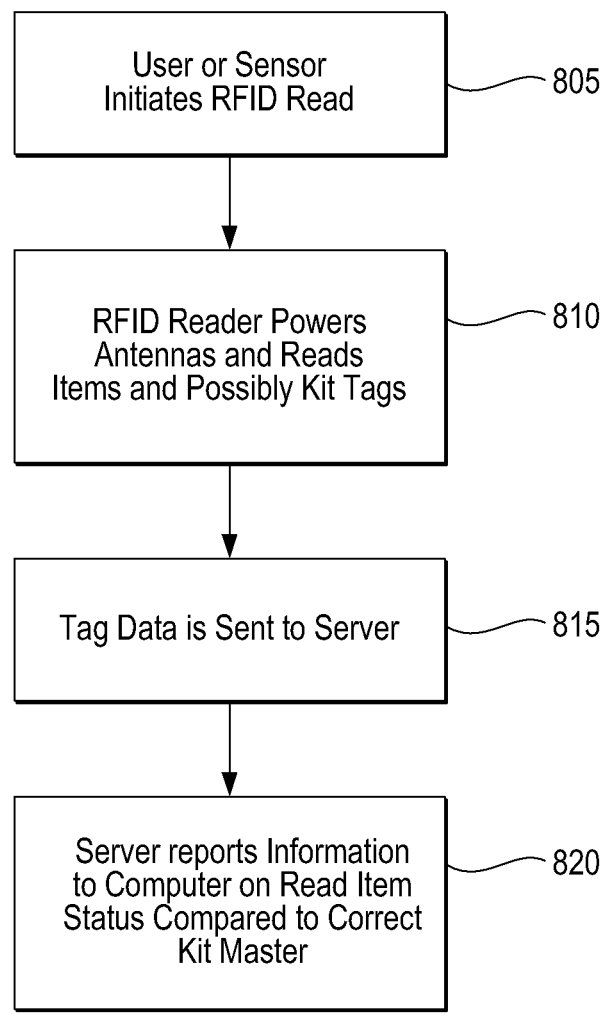
FIGS. 17A and 17B are flowcharts illustrating methods of operating the system of FIG. 1 according to an embodiment of the inventive concept.
Figure 17B:
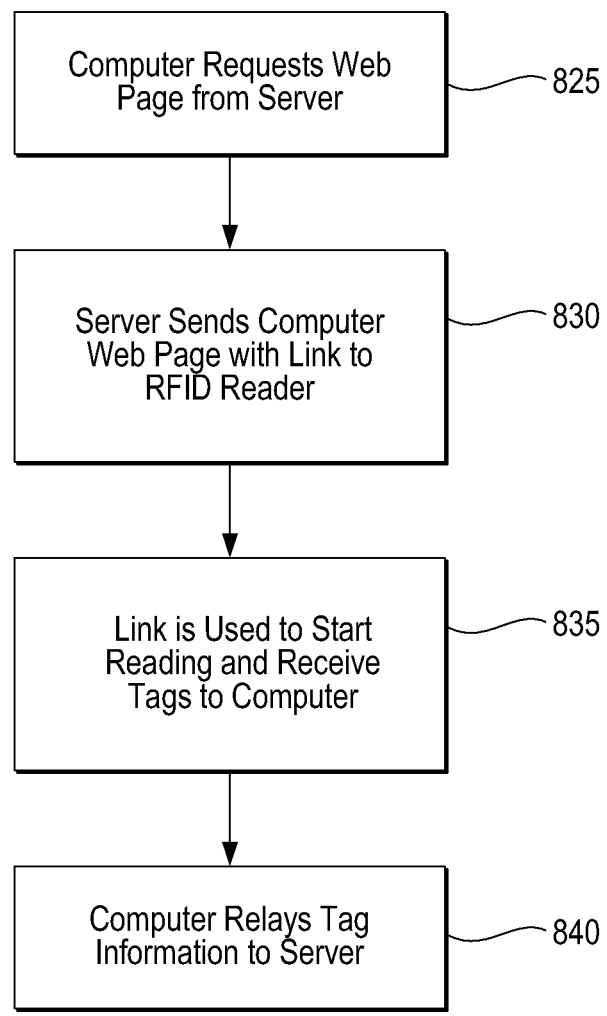

FIGS. 17A and 17B are flowcharts illustrating methods of operating kit management system 100 according to an embodiment of the inventive concept. In particular, FIG. 17A shows a method that can be used to implement step 515 of FIG. 14, and FIG. 17B shows a method that can be used to implement parts of the method of FIG. 17A.

Referring to FIG. 17A, a user or sensor initiates an RFID read operation (805). This can be accomplished, for instance, by merely placing kit 105 in RFID reading station 110, or by actuating specific controls on a user interface. In the read operation, RFID reader 305 powers antennas of RFID tags in kit 105, and it reads item tags and a kit tag, if present (810). The read operation may be used to perform an initial inventory of kit 105 following its assembly, or it can used for a re-inventory following use. Next, tag data is sent to a server in information processing system 115 or elsewhere (815). Finally, the server reports information to a user via an interface such as a computer display or a computer-generated printout (820).

Referring to FIG. 17B, steps 805 and 815 can be performed through the use of a web interface such as a web browser. For example, in some embodiments, a user directs a computer to request a web page from a server (825). This is typically accomplished through a web browser and it can be done in an encrypted or non-encrypted manner. For instance, the computer can communicate with the server using an encrypted protocol such as the secure sockets layer (SSL) protocol.

Next, the server returns instructions on how to scan which could take the form of a link allowing control of the RFID reader (830). In the example using a link, the user clicks on the link to start a read operation, and the RFID reader then captures tag information from kit 105 and transmits it to the computer (835). Finally, the computer relays the tag information to the server for validation, storage, and/or other forms of processing (840).

The server typically stores kit-related information such as master templates, item master templates, and information regarding individual kits and items, as in the example of FIG. 13. This information can be compared with the tag information relayed to the server in step 840, and then based on the comparison the server may generate a report on the status of the kit, such as whether any items are absent or whether any items have been erroneously included in the kit. The report may also include information relating to the expiration status of the items in kit 105, such as whether the items are expired or near expiration, or a summary of the expiration status of a set of items or the kit as a whole. The report may also include a charge sheet including the status of each item, such as its expiration date, which items have expired, which items are about to expire, and which item is going to expire next. In general, the information included in the report may be data that was read from a kit, item, or other source, or it may be data that was calculated based on rules, inputs, or other criteria.

Figure 18:
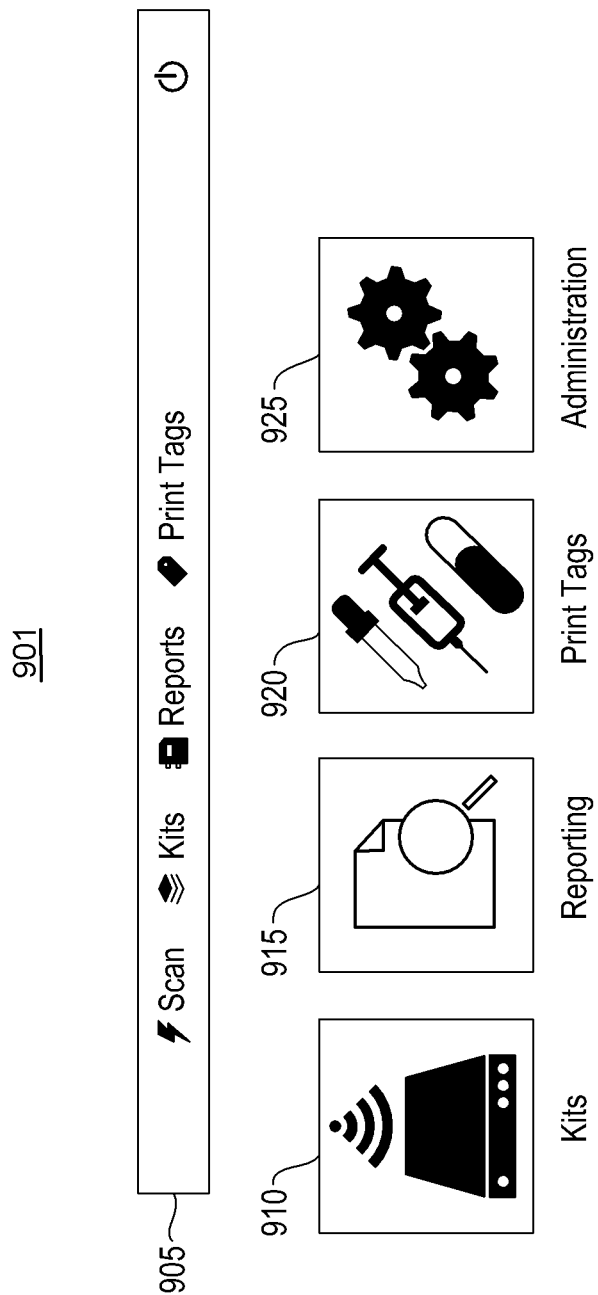
FIG. 18 shows an interface that can be used to control the system of FIG. 1 according to an embodiment of the inventive concept.

FIG. 18 shows an interface 901 that can be used to control system 100 according to an embodiment of the inventive concept. For example, interface 901 can be used to control various aspects of the methods illustrated in FIGS. 14 through 17. Interface 901 is typically accessed through a display connected to a computer or server such as those illustrated in FIG. 13.

Referring to FIG. 18, interface 901 comprises interactive graphical user interface (GUI) components including a menu bar 905 and buttons 910 through 925. These features allow a user to initiate various kit-related procedures, such as scanning a kit that has been placed in an RFID reading station, generating reports based on kit information, printing RFID tags for a kit, and performing administrative tasks. For example, a user may press button 910 (or alternatively, a scan button in menu bar 905) to initiate a read operation of RFID reading station 110 after kit 105 has been placed in a designated reading location such as a metal box. The user may press button 915 to generate a report comprising information similar to that illustrated in FIG. 11C. The user may press button 920 to initiate a procedure for capturing item information and printing RFID tags. Finally, the user may press button 925 to access various administrative controls for system 100 or interface 901.

FIG. 19 shows a report 1001 generated for a pharmacy kit using system 100 according to an embodiment of the inventive concept. Report 1001 corresponds to a pediatric emergency drug tray, which is a type of kit comprising items used for common pediatric emergencies. Such a kit can be deployed to a hospital emergency room, for example.

Referring to FIG. 19, report 1001 comprises a portion 1005 indicating the type of kit for which the report was generated, as well as the total number of items in the kit. In this example, the kit comprises 51 total items. Report 1001 further comprises a portion 1010 indicating the number of extra and missing items in the kit, as well as the number of expired or soon to expire items. In this example, one item is missing and two items are near expiration. The soon-to-expire items are listed as two containers of Procainamide Hydrochloride, which expire on Oct. 1, 2012. The date range of soon-to-expire items can be set arbitrarily, for example, using administrative tools accessible through button 925 in interface 901. Nevertheless, the date range is typically established in consideration of factors such as the anticipated delay between deployment of the kit and its use, as well as any regulatory considerations, such as rules from the board-of-pharmacy requirements or the joint commission (TJC).

Report 1001 also includes a portion 1015 indicating the date of a most recent scan, a portion 1020 showing additional details for the soon-to-expire items, and a portion 1025 showing additional details for missing items.

FIG. 20 shows another report 1100 generated for a pharmacy kit using system 100 according to an embodiment of the inventive concept. Report 1100 corresponds to a demonstration kit, which is a type of kit comprising items used for common pediatric emergencies. Such a kit can be deployed to a hospital emergency room, for example.

Report 1100 comprises a portion 1105 indicating the type of the kit and the total number of items in the kit. In this example, the kit comprises 26 total items. Report 1100 further comprises a portion 1010 indicating the number of extra and missing items in the kit, an entity to be billed for used items, and the number of expired or soon to expire items. In this example, there are two extra items, one expired item, and one soon-to-expire item. The entity to be billed is listed as KRE1981. The expired item is a box of Protopic, which is listed as having expired on Sep. 28, 2012.

Report 1100 further comprises a portion 1115 indicating the date of a most recent scan, a portion 1120 showing additional details for the expired items, a portion 1125 showing additional details for the soon-to-expire items, and a portion 1130 showing additional details for the extra items. Report 1100 still further comprises a portion 1135 indicating a current location of the kit and providing a "check out" button for assigning the kit to a specific location or person. In this example, the kit is currently assigned to the location "Central Pharmacy".

Figure 21:
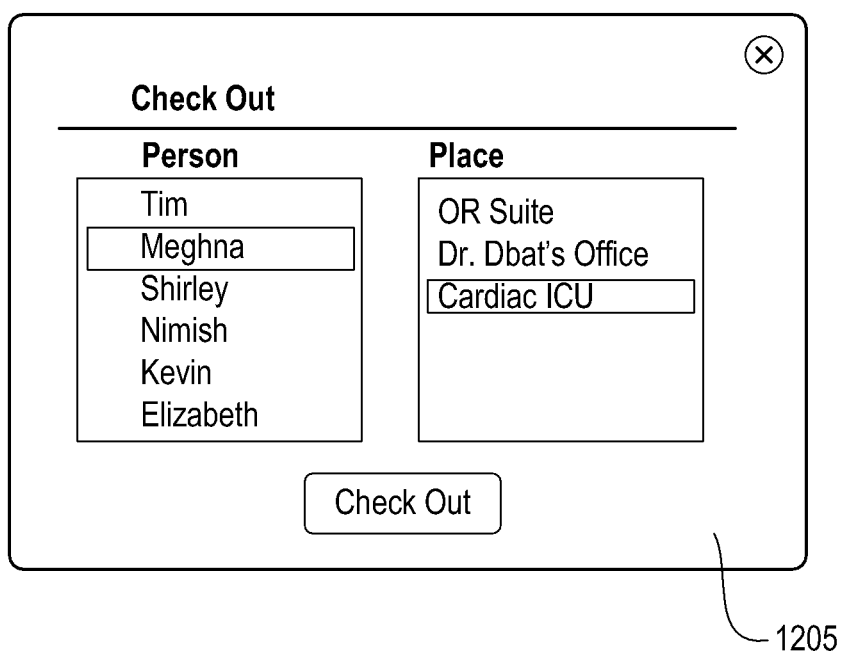
FIG. 21 shows an interface for checking out a kit to a user or location according to an embodiment of the inventive concept.

FIG. 21 shows an interface 1200 for checking out a kit to a user or location according to an embodiment of the inventive concept. Interface 1200 can be invoked, for instance, using the check out button in area 1135 of FIG. 20. In response to a user pressing the check out button, a dialog box 1205 appears within interface 1200. Dialog box 1205 allows a user to select a person or place to whom the kit may be assigned. This selection can be made, for example, as the kit is placed in possession of the selected person or an authorized delivery agent. Information regarding the selected person and location can then be stored in system 100 to facilitate subsequent recovery or further monitoring of the kit.

FIGS. 22A and 22B show interfaces 1300A and 1300B used to generate and view reports for pharmacy kits according to an embodiment of the inventive concept. In particular, FIG. 22A shows an example of an interface where a user has selected to view a report of kits that need re-working, and FIG. 22B shows an example of an interface where a user has selected to view a report of kits containing a specific lot number.

Referring to FIG. 22A, interface 1300A comprises a first area 1305A where a user selects a type of report to be generated. In this example, the user has selected from a drop down menu to generate a report of kits that need re-working. Once the selection is made the drop down menu, first area 1305A is further populated with options of details to include in the report. In this example, the options allow the user to select whether the report should include surplus items, shortages, expired items, expiring items, or all segments of the kit.

Interface 1300A further comprises a second area 1310A for displaying the report. According to the report in area 1310A, system 100 has information on two kits satisfying the specified options. In particular, a demo kit has a shortage of nasal spray, and it has a soon-to-expire container of Gentamicin Sulfate. A bandage kit has shortages of small, medium, and large bandages.

Referring to FIG. 22B, interface 1300B comprises a first area 1305B where a user selects the type of report to be generated. In this example, the user has selected from the drop down menu to generate a report of kits containing a specific item or lot number. Based on this selection, first area 1305B is populated with a form allowing the user to enter all or part of a lot number or other information for identifying the item. In the example of FIG. 22B, the user has entered a lot number.

Interface 1300B further comprises a second area 1310B for displaying the report. According to the report in area 1310B, a demo kit includes an item with the lot number specified in second area 1310A. Notably, in the example of FIG. 22B, only a partial lot number is entered first area in 1305B, so second area 1310B displays information related to items that begin with the partial lot number. However, system 100 could be modified to use the exact lot number only. It could also be modified to use multiple lot numbers.

In addition to generating reports such as those illustrated in FIGS. 19 through 13, system 100 may also generate reports on kit locations. Such locations can be determined, for example, through automatic kit tracking or some other mechanism. Moreover, system 100 may also provide mechanisms for automatically tracking inventory in the kits and the usage of items based on usage data. For example, by analyzing usage data of different items, system 100 could determine the level inventory to meet minimum requirements of all kits in a facility or a target level of inventory to be maintained. For example, if a type of kit requires a bottle of ibuprofen and the facility has 20 kits of that type, the facility has a minimum requirement of 20 bottles of ibuprofen. If the facility uses 19 bottles of ibuprofen during a specified time (e.g., a month), system 100 could then estimate or predict when the facility will run out of the current stock of ibuprofen. Accordingly, system 100 can be used to predict where inventory shortages may occur and then alert relevant personnel of potential existing or upcoming inventory shortages.

System 100 may also automatically inventory items in pharmacy kits to determine where anything is missing, extra, expired, or near expired. This can reduce the chance of manual kit stocking errors or related medical errors in a hospital or other facility. System 100 may also automatically find items for recall in the hospital or emergency medical field kits.

As indicated by the foregoing, embodiments of the inventive concept provide various systems and methods for managing pharmacy kits using multiple acceptance criteria for pharmacy kit segments. These and other embodiments may potentially improve the efficiency and accuracy of kit stocking procedures, kit verification procedures, and related reporting procedures, among other things.

The foregoing is illustrative of embodiments and is not to be construed as limiting thereof. Although a few embodiments have been described, those skilled in the art will readily appreciate that many modifications are possible in the embodiments without materially departing from the scope of the inventive concept. Accordingly, all such modifications are intended to be included within the scope of the inventive concept as defined in the claims.

What is claimed is:

1. A method of managing a pharmacy kit, comprising:
causing an antenna coupled to a pharmacy kit container to emit a radio signal at least within the pharmacy kit container;
receiving tag information of a plurality of radio frequency identification (RFID) tags coupled to a plurality of medicinal containers based at least in part on the antenna emitting the radio signal at least within the pharmacy kit container,
wherein the pharmacy kit container provides electromagnetic shielding,
wherein the plurality of medicinal containers are configured to store a plurality of medications,
wherein the plurality of RFID tags are associated with a pharmacy kit located within the pharmacy kit container and are associated with medication data of the plurality of medications,
wherein a first RFID tag of the plurality of RFID tags is coupled to a first medicinal container of the plurality of medicinal containers and the first medicinal container is configured to store a first medication of the plurality of medications, and
wherein the first RFID tag is associated with first medication data of the first medication, the first medication data comprising at least an identifier of the first medication and a concentration of the first medication;
determining whether a kit stocking contingency has occurred with respect to a segment of the pharmacy kit based at least in part on the received tag information, wherein the segment identifies a medication type and medication concentration that forms at least a portion of the pharmacy kit;
based at least in part on a determination that the kit stocking contingency has not occurred, determining whether the segment has been satisfactorily stocked according to a first acceptance criterion, wherein determining whether the segment has been satisfactorily stocked according to the first acceptance criterion comprises comparing the medication data associated with the plurality of RFID tags with the segment to determine whether at least one medicinal container of the plurality of medicinal containers stores the medication type and medication concentration identified by the segment;
based at least in part on a determination that the kit stocking contingency has occurred, determining whether the segment has been satisfactorily stocked according to a second acceptance criterion different from the first acceptance criterion, wherein determining whether the segment has been satisfactorily stocked according to the second acceptance criterion comprises comparing the medication data associated with the plurality of RFID tags with the segment to determine whether the at least one medicinal container stores the medication type identified by the segment and a substitute medication concentration; and
causing a display to display information regarding whether the segment has been satisfactorily stocked according to at least one of the first acceptance criterion or the second acceptance criterion.

2. The method of claim 1, wherein the kit stocking contingency comprises a shortage of at least one medication corresponding to the first acceptance criterion.

3. The method of claim 2, wherein determining whether the kit stocking contingency has occurred comprises receiving a shortage notification for the at least one medication corresponding to the first acceptance criterion.

4. The method of claim 1, wherein the first and second acceptance criterion specify different types of items that can be used to stock the segment.

5. The method of claim 4, wherein the different types of items comprise different types of medication.

6. The method of claim 1, wherein the first acceptance criterion specifies a size of medication that can be used to satisfactorily stock the segment, and the second acceptance criterion specifies an alternative size of medication that can be used to satisfactorily stock the segment.

7. The method of claim 1, wherein the first acceptance criterion specifies a quantity of medication that can be used to satisfactorily stock the segment, and the second acceptance criterion specifies an alternative quantity of medication that can be used to satisfactorily stock the segment.

8. The method of claim 1, further comprising:
 determining whether an additional kit stocking contingency has occurred; and
 based at least in part on determining that the additional kit stocking contingency has occurred, determining whether the segment of the pharmacy kit has been satisfactorily stocked according to at least one additional acceptance criterion different from the first and second acceptance criterion.

9. The method of claim 8, wherein the second acceptance criterion and the at least one additional acceptance criterion are ranked in order of user preference.

10. The method of claim 1, further comprising receiving user input defining one or more rules for determining, based on the first acceptance criterion or the second acceptance criterion, whether the segment is satisfactorily stocked.

11. A system, comprising:
 a reading station, comprising:
  a pharmacy kit container formed of a material designed to provide electromagnetic shielding, and
  an antenna coupled to the pharmacy kit container; and
 a non-transitory computer-readable medium storing computer-executable instructions that when executed by one or more processors cause the one or more processors to:
  cause the antenna to emit a radio signal at least within the pharmacy kit container;
  receive tag information of a plurality of radio frequency identification (RFID) tags coupled to a plurality of medicinal containers based at least in part on the antenna emitting the radio signal at least within the pharmacy kit container, the plurality of medicinal containers configured to store a plurality of medications, wherein the plurality of RFID tags are associated with a pharmacy kit located within the pharmacy kit container and are associated with medication data of the plurality of medications,
   wherein a first RFID tag of the plurality of RFID tags is coupled to a first medicinal container of the plurality of medicinal containers and the first medicinal container is configured to store a first medication of the plurality of medications, and
   wherein the first RFID tag is associated with first medication data of the first medication, the first medication data comprising at least an identifier of the first medication and a concentration of the first medication;
  determine whether a kit stocking contingency has occurred with respect to a segment of the pharmacy kit based at least in part on the received tag information, wherein the segment identifies a medication type and medication concentration that forms at least a portion of the pharmacy kit;
  based at least in part on a determination that the kit stocking contingency has not occurred, determine whether the segment has been satisfactorily stocked according to a first acceptance criterion, wherein to determine whether the segment has been satisfactorily stocked according to the first acceptance criterion the computer-executable instructions cause the one or more processors to compare the medication data associated with the plurality of RFID tags with the segment to determine whether at least one medicinal container of the plurality of medicinal containers stores the medication type and medication concentration identified by the segment;
  based at least in part on a determination that the kit stocking contingency has occurred, determine whether the segment has been satisfactorily stocked according to a second acceptance criterion different from the first acceptance criterion, wherein to determine whether the segment has been satisfactorily stocked according to the second acceptance criterion the computer-executable instructions cause the one or more processors to compare the medication data associated with the plurality of RFID tags with the segment to determine whether the at least one medicinal container stores the medication type identified by the segment and a substitute medication concentration; and
  cause a display to display information regarding whether the segment has been satisfactorily stocked according to at least one of the first acceptance criterion or the second acceptance criterion.

12. The system of claim 11, wherein the kit stocking contingency comprises a shortage of at least one medication corresponding to the first acceptance criterion.

13. The system of claim 12, to determine whether the kit stocking contingency has occurred the computer-executable instructions cause the one or more processors to receive a shortage notification for the at least one medication corresponding to the first acceptance criterion.

14. The system of claim 11, wherein the first and second acceptance criterion specify different types of items that can be used to stock the segment.

15. The system of claim 14, wherein the different types of items comprise different types of medication.

16. The system of claim 11, wherein the first acceptance criterion specifies a size of medication that can be used to satisfactorily stock the segment, and the second acceptance criterion specifies an alternative size of medication that can be used to satisfactorily stock the segment.

17. The system of claim 11, wherein the first acceptance criterion specifies a quantity of medication that can be used to satisfactorily stock the segment, and the second acceptance criterion specifies an alternative quantity of medication that can be used to satisfactorily stock the segment.

18. The system of claim 11, wherein the computer-executable instructions further cause the one or more processors to:

determine whether an additional kit stocking contingency has occurred; and based at least in part on a determination that the additional kit stocking contingency has occurred, determine whether the segment of the pharmacy kit has been satisfactorily stocked according to one or more additional acceptance criterion different from the first and second acceptance criterion.

19. The system of claim 11, wherein the reading station comprises the non-transitory computer-readable medium.

20. The system of claim 11, wherein the reading station is communicatively coupled to the non-transitory computer-readable medium via a network.

* * * * *